(12) United States Patent
Rebstock et al.

(10) Patent No.: US 9,743,665 B2
(45) Date of Patent: Aug. 29, 2017

(54) FUNGICIDAL 3-{PHENYL[HETEROCYCLYLMETHOXY)IMINO]METHYL}-OXADIAZOLONE DERIVATIVES

(71) Applicant: BAYER CROPSCIENCE AKTIENGESELLSCHAFT, Monheim (DE)

(72) Inventors: Anne-Sophie Rebstock, Wuppertal (DE); Christophe Dubost, Charbonnieres les bains (FR); Pierre-Yves Coqueron, Lyons (FR); Simon Maechling, Lyons (FR); Helene Lachaise, Lyons (FR); Philippe Rinolfi, Chatillon D Azergues (FR); Ulrike Wachendorff-Neumann, Neuwied (DE); Christoph Andreas Braun, Duesseldorf (DE)

(73) Assignee: BAYER CROPSCIENCE AKTIENGESELLSCHAFT (DE)

( * ) Notice: Subject to any disclaimer, the term of this patent is extended or adjusted under 35 U.S.C. 154(b) by 0 days.

(21) Appl. No.: 14/767,445

(22) PCT Filed: Mar. 3, 2014

(86) PCT No.: PCT/EP2014/054024
§ 371 (c)(1),
(2) Date: Aug. 12, 2015

(87) PCT Pub. No.: WO2014/135477
PCT Pub. Date: Sep. 12, 2014

(65) Prior Publication Data
US 2016/0007607 A1    Jan. 14, 2016

Related U.S. Application Data

(60) Provisional application No. 61/803,333, filed on Mar. 19, 2013.

(30) Foreign Application Priority Data

Mar. 4, 2013 (EP) .................................. 13356002

(51) Int. Cl.
| | | |
|---|---|---|
| A61K 31/425 | (2006.01) |
| A01N 43/82 | (2006.01) |
| C07D 231/38 | (2006.01) |
| C07D 413/12 | (2006.01) |
| C07D 417/12 | (2006.01) |
| C07D 277/22 | (2006.01) |
| C07D 277/32 | (2006.01) |
| C07D 277/40 | (2006.01) |
| C07D 277/56 | (2006.01) |
| A01N 43/56 | (2006.01) |
| A01N 43/78 | (2006.01) |
| C07D 277/24 | (2006.01) |
| C07D 417/14 | (2006.01) |

(52) U.S. Cl.
CPC ............. *A01N 43/82* (2013.01); *A01N 43/56* (2013.01); *A01N 43/78* (2013.01); *C07D 231/38* (2013.01); *C07D 277/22* (2013.01); *C07D 277/24* (2013.01); *C07D 277/32* (2013.01); *C07D 277/40* (2013.01); *C07D 277/56* (2013.01); *C07D 413/12* (2013.01); *C07D 417/12* (2013.01); *C07D 417/14* (2013.01)

(58) Field of Classification Search
None
See application file for complete search history.

(56) References Cited

U.S. PATENT DOCUMENTS

| | | |
|---|---|---|
| 8,981,111 B2 | 3/2015 | Beier et al. |
| 9,000,012 B2 | 4/2015 | Beier et al. |
| 9,090,600 B2 * | 7/2015 | Braun ..................... A01N 43/82 |
| 2014/0206726 A1 | 7/2014 | Benting et al. |

FOREIGN PATENT DOCUMENTS

| | | |
|---|---|---|
| EP | 1038874 A1 | 9/2000 |
| EP | 1184382 A1 | 3/2002 |
| WO | 2009130193 A1 | 10/2009 |
| WO | 2011080254 A2 | 7/2011 |
| WO | 2013026836 A1 | 2/2013 |

OTHER PUBLICATIONS

International Search Report from Corresponding PCT/EP2014/054024, mailed Mar. 25, 2014.

* cited by examiner

*Primary Examiner* — Craig Ricci
(74) *Attorney, Agent, or Firm* — McBee Moore Woodward & Vanik IP, LLC

(57) ABSTRACT

The present invention provides 4-substituted-3-{phenyl[(heterocyclylmethoxy)imino]methyl}-1,2,4-oxadiazol-5(4H)-one derivatives of formula (I)

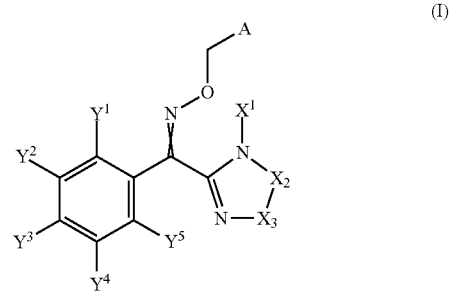

Wherein A and $X^1$ to $X^3$ and Y1 to $Y^5$ represent various substituents.

10 Claims, No Drawings

FUNGICIDAL 3-{PHENYL[HETEROCYCLYLMETHOXY)IMINO]METHYL}-OXADIAZOLONE DERIVATIVES

CROSS REFERENCE TO RELATED APPLICATIONS

This application is a §371 National Stage Application of PCT/EP2014/054024, filed 3 Mar. 2014, which claims priority to EP 13356002.9, filed 4 Mar. 2013 and U.S. 61/803,333, filed 19 Mar. 2013.

BACKGROUND

Field of the Invention

The present invention relates to 4-substituted-3-{phenyl[(heterocyclylmethoxy)imino]methyl}-1,2,4-oxadiazol-5(4H)-one derivatives, their process of preparation, their use as fungicide active agents, particularly in the form of fungicide compositions, and methods for the control of phytopathogenic fungi, notably of plants, using these compounds or compositions.

Description of Related Art

In European patent application n° 1184382, there are disclosed certain heterocyclyloxime derivatives of the following chemical structure:

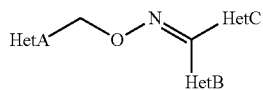

that are excluded from the scope of the present invention.

In patent application WO2009/130193, there are disclosed certain hydroximoyl-heterocycles derivatives of the following chemical structure:

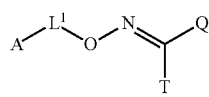

wherein Q is a phenyl ring, L1 a methylene linker and A an heterocycle, and T is

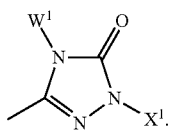

Said compounds are not part of the scope of the present invention.

SUMMARY

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides 3-{phenyl[(heterocyclylmethoxy)imino]methyl}-oxadiazolone derivatives of formula (I)

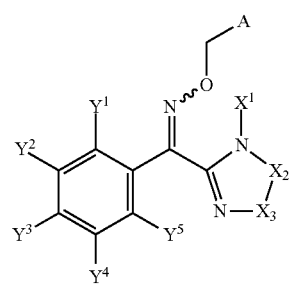

wherein $X^1$ represents a hydrogen atom, a formyl group, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_2$-$C_8$-alkynyl, substituted or non-substituted $C_1$-$C_8$-alkylcarbonyl;

$X^2$ and $X^3$ represents O or C=O, provided that $X^2$ represents O when $X^3$ is C=O and $X^2$ represents C=O when $X^3$ is O A is selected in the list consisting of $A^1$ to $A^{25}$:

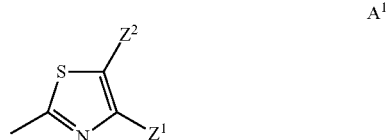

$A^1$

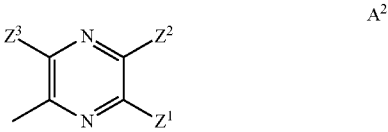

$A^2$

$A^3$

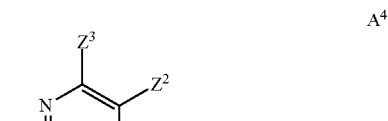

$A^4$

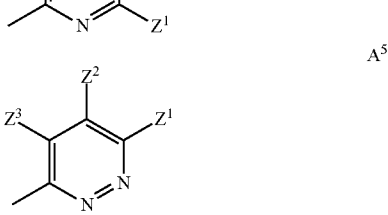

$A^5$

A⁶ 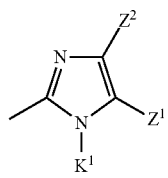

A⁷ 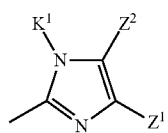

A⁸ 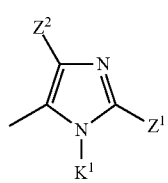

A⁹ 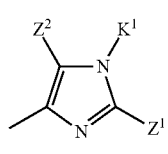

A¹⁰ 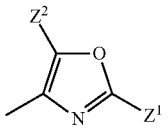

A¹¹ 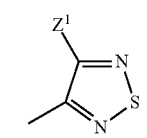

A¹² 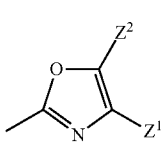

A¹³ 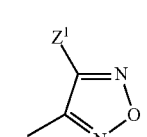

A¹⁴ 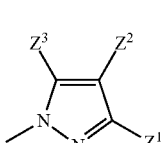

A¹⁵ 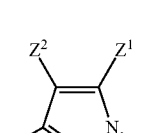

A¹⁶ 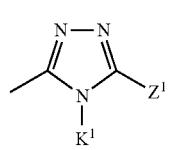

A¹⁷ 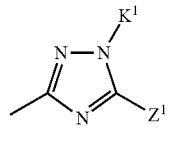

A¹⁸ 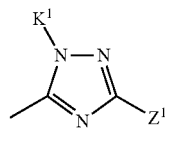

A¹⁹ 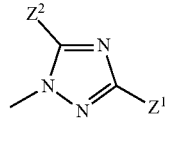

A²⁰ 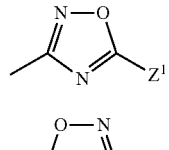

A²¹ 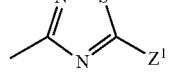

A²² 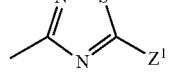

A²³ 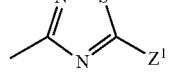

A²⁴ 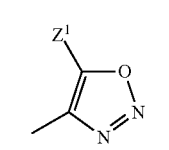

A²⁵ 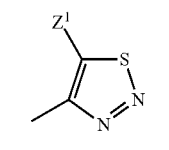

wherein $Z^1$ represents a hydrogen atom, a halogen atom, a nitro group, an amino group, an hydroxyamino group, a hydroxy group, a cyano group, a carboxylic acid, a sulfenyl group, a formyl group, a substituted or non-substituted carbaldehyde O—($C_1$-$C_8$-alkyl)oxime, a formyloxy group, a carbamoyl group, a N-hydroxycarbamoyl group, sulfenylthioylamino, a pentafluoro-$\lambda^6$-sulfenyl group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_3$-alkylamino)-amino group, substituted or non-substituted N—$C_1$-$C_8$-alkyl- ($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted $C_3$-$C_8$-cycloalkyl, substituted or non-substituted $C_2$-$C_8$-alkenyl, substituted or non-substituted $C_2$-$C_8$-alkynyl, substituted or non-substituted aryl-$C_2$-$C_8$-alkynyl, substituted or non-substituted $C_3$-$C_8$-cycoalkyl-$C_2$-$C_8$-alkynyl, substituted or non-substituted $C_1$-$C_8$-alkoxy, substituted or non-substituted $C_2$-$C_8$-alkenyloxy, substituted or non-substituted $C_3$-$C_8$-alkynyloxy, substituted or non-substituted $C_1$-$C_8$-alkoxycarbonyl, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—$C_1$-$C_8$-alkyl-carbamoyl, substituted or non-substituted N—$C_3$-$C_8$-cycloalkyl-carbamoyl, substituted or non-substituted N-aryl-carbamoyl, substituted or non-substituted N,N'-di-$C_1$-$C_8$-alkyl-carbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkylcarbonyloxy, substituted or non-substituted N—$C_1$-$C_8$-alkylaminocarbonyloxy, substituted or non-substituted N,N'-di-$C_1$-$C_8$-alkylaminocarbonyloxy, substituted or non-substituted N—$C_1$-$C_8$-alkylcarbamothioyl, substituted or non-substituted N,N'-di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_1$-$C_8$-alkylsulfinyl, substituted or non-substituted $C_1$-$C_8$-alkylsulfonyl, substituted or non-substituted $C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted phenoxy, substituted or non-substituted phenylsulfenyl, substituted or non-substituted aryl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-alkylsulfonylamino, substituted or non-substituted $C_1$-$C_8$-alkoxysulfonylamino, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy, substituted or non-substituted (N-hydroxy-$C_1$-$C_6$-alkanimidoyl)amino, substituted or non-substituted (N—$C_1$-$C_6$-alkoxy-$C_1$-$C_6$-alkanimidoyl)amino, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, substituted or non-substituted $C_3$-$C_{10}$-cycloalkyl-$C_1$-$C_8$-alkylamino, substituted or non-substituted aryl-$C_1$-$C_3$-alkylamino, substituted or non-substituted $C_1$-$C_8$-alkoxy-$C_1$-$C_8$-alkylamino, or a group of formula QC(=U)NR$^a$— wherein

Q represents a hydrogen atom, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_3$-$C_8$-cycloalkenyl, substituted or non-substituted $C_2$-$C_3$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylamino, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted aryl, substituted or non-substituted heterocyclyl, substituted or non-substituted $C_5$-$C_{12}$-fused bicycloalkyl, substituted or non-substituted $C_5$-$C_{12}$-fused bicycloalkenyl, substituted or non-substituted $C_5$-$C_{12}$-benzofused carbocyclyl, substituted or non-substituted $C_5$-$C_{12}$-benzofused heterocyclyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, substituted or non-substituted $C_5$-$C_{12}$-benzofused heterocyclyloxy, substituted or non-substituted $C_3$-$C_8$-cycloalkyl-$C_1$-$C_8$-alkyl, substituted or non-substituted $C_3$-$C_8$-cycloalkyl-$C_1$-$C_8$-alkoxy, substituted or non-substituted $C_3$-$C_8$-cycloalkoxy-$C_1$-$C_8$-alkyl, substituted or non-substituted heterocyclyl-$C_1$-$C_8$-alkyl, substituted or non-substituted aryl-$C_1$-$C_3$-alkyl, substituted or non-substituted aryl-$C_1$-$C_8$-alkoxy, substituted or non-substituted aryloxy-$C_1$-$C_8$-alkyl, substituted or non-substituted $C_1$-$C_8$-alkoxy-$C_1$-$C_8$-alkyl, substituted or non-substituted $C_1$-$C_8$-alkoxy-$C_1$-$C_8$-alkoxy, substituted or non-substituted aryloxy-$C_1$-$C_8$-alkoxy, substituted or non-substituted $C_1$-$C_8$-alkoxyaryloxy, substituted or non-substituted $C_1$-$C_8$-alkoxy-$C_1$-$C_8$-alkyl, substituted or non-substituted aryl-$C_1$-$C_8$-alkynyloxy, substituted or non-substituted $C_1$-$C_8$-alkylaryl, substituted or non-substituted $C_1$-$C_8$-alkoxyaryl, substituted or non-substituted $C_1$-$C_8$-alkoxy-$C_1$-$C_8$-alkoxy, substituted or non-substituted $C_1$-$C_8$-alkyl-$C_3$-$C_8$-cycloalkoxy, substituted or non-substituted $C_1$-$C_8$-alkyl-$C_3$-$C_8$-cycloalkyl;

U represents a oxygen atom or a sulfur atom;

R$^a$ represents a hydrogen atom, a hydroxy group, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_2$-$C_8$-alkynyl, substituted or substituted or non-substituted $C_5$-$C_{12}$-fused bicycloalkyl, substituted or non-substituted $C_5$-$C_{12}$-fused bicycloalkenyl, substituted or non-substituted aryl, or substituted or non-substituted heterocyclyl, substituted or non-substituted $C_1$-$C_8$-alkylcarbonyl, substituted or non-substituted aryloxycarbonyl, substituted or non-substituted $C_1$-$C_8$-alkoxycarbonyl;

$Z^2$ and $Z^3$ independently represent a hydrogen atom, a halogen atom, substituted or non-substituted $C_1$-$C_8$-alkyl, substituted or non-substituted $C_3$-$C_8$-cycloalkyl, substituted or non-substituted $C_2$-$C_8$-alkenyl, substituted or non-substituted $C_2$-$C_8$-alkynyl, substituted or non-substituted $C_1$-$C_8$-alkoxy;

$K^1$ represents a hydrogen atom, a formyl group, substituted or non-substituted $C_1$-$C_8$-alkyl, substituted or non-substituted $C_3$-$C_8$-cycloalkyl, substituted or non-substituted $C_1$-$C_8$-alkylcarbonyl;

$Y^1$ to $Y^5$ independently represent a hydrogen atom, a halogen atom, a nitro group, a cyano group, a substituted or non-substituted carbaldehyde O—($C_1$-$C_8$-alkyl)oxime, a pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted phenoxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

as well as salts, N-oxides, metallic complexes and metalloidic complexes thereof or (E) and (Z) isomers and mixtures thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

Notably, the stereostructure of the oxime moiety present in the compounds of formula (I) includes (E) or (Z) isomer, and these stereoisomers form part of the present invention.

DETAILED DESCRIPTION OF A PREFERRED EMBODIMENT

According to the invention, the following generic terms are generally used with the following meanings:

halogen means fluorine, chlorine, bromine or iodine;
heteroatom can be nitrogen, oxygen or sulfur;
unless indicated otherwise, a group or a substituent that is substituted according to the invention can be substituted by one or more of the following groups or atoms: a halogen atom, a nitro group, a hydroxy group, a cyano group, an amino group, a sulfenyl group, a pentafluoro-$\lambda^6$-sulfenyl group, a formyl group, a carbaldehyde O—($C_1$-$C_8$-alkyl)oxime, a formyloxy group, a formylamino group, a formylamino group, a (hydroxyimino)-$C_1$-$C_6$-alkyl group, a $C_1$-$C_8$-alkyl, a tri($C_1$-$C_8$-alkyl) silyl, $C_3$-$C_8$-cycloalkyl, $C_3$-$C_8$-cycloalkenyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfenyl, a $C_1$-$C_8$-halogenoalkylsulfenyl having 1 to 5 halogen atoms, a $C_2$-$C_8$-halogenoalkenyloxy having 1 to 5 halogen atoms, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, $C_1$-$C_8$-alkoxycarbonylamino, $C_1$-$C_8$-halogenoalkoxycarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_3$-alkoxyalkyl, $C_1$-$C_8$-halogenoalkoxyalkyl having 1 to 5 halogen atoms, benzyloxy, benzylsulfenyl, benzylamino, phenoxy, phenylsulfenyl, or phenylamino, an aryl group, an heterocyclyl group; or a group or a substituent that is substituted according to the invention can be substituted in a way that substituting groups form together a substituted or non-substituted, saturated or partially saturated 3-, 4-, 5-, 6-, 7-, 8-, 9-, 10-, or 11-membered cycle, which can be a carbocycle or a heterocycle comprising up to 4 heteroatoms selected from the list consisting of N, O, and S the term "aryl" means phenyl or naphthyl;

the term "heterocyclyl" means fused or non-fused, saturated or unsaturated, 4-, 5-, 6-, 7-, 8-, 9-, 10-, 11- or 12-membered ring comprising up to 4 heteroatoms selected in the list consisting of N, O, S.

Where a compound of the invention can be present in tautomeric form, such a compound is understood hereinabove and hereinbelow also to include, where applicable, corresponding tautomeric forms, even when these are not specifically mentioned in each case.

Preferred compounds of formula (I) according to the invention are those wherein $X^1$ represents a hydrogen atom, substituted or non-substituted $C_1$-$C_8$-alkyl, substituted or non-substituted $C_3$-$C_8$-cycloalkyl or a substituted or non-substituted $C_2$-$C_8$-alkenyl.

More preferred compounds of formula (I) according to the invention are those wherein $X^1$ represents a hydrogen atom, a methyl group, an ethyl group, a n-propyl group, an isopropyl group or a cyclopropyl group.

Even more preferred compounds of formula (I) according to the invention are those wherein $X^1$ represents a hydrogen atom or a methyl group.

Other preferred compounds of formula (I) according to the invention are those wherein A is selected in the list consisting of $A^1$ to $A^{15}$.

More preferred compounds of formula (I) according to the invention are those wherein A is selected in the list consisting of $A^1$, $A^3$, $A^4$ and $A^{14}$.

Even more preferred compounds of formula (I) according to the invention are those wherein A is selected in the list consisting of $A^1$ and $A^{14}$.

Other preferred compounds of formula (I) according to the invention are those wherein $Z^1$ represents a hydrogen atom, a halogen atom, a nitro group, an amino group, a carboxylic acid, an hydroxyamino group, a substituted or non-substituted carbaldehyde O—($C_1$-$C_8$-alkyl)oxime, substituted or non-substituted $C_1$-$C_8$-alkoxyamino group, substituted or non-substituted $C_1$-$C_8$-alkoxycarbonyl group, a substituted or non-substituted (hydroxyimino)-$C_1$-$C_6$-alkyl group, substituted or non-substituted $C_2$-$C_8$-alkenyl, substituted or non-substituted $C_2$-$C_8$-alkynyl, substituted or non-substituted aryl-$C_2$-$C_8$-alkynyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted (N-hydroxy-$C_1$-$C_6$-alkanimidoyl)amino, substituted or non-substituted (N—$C_1$-$C_6$-alkoxy-$C_1$-$C_6$-alkanimidoyl)amino, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula QC(=U)$R^a$—

More preferred compounds of formula (I) according to the invention are those wherein $Z^1$ represents a hydrogen atom, a halogen atom, a nitro group, an amino group, a carboxylic acid, substituted or non-substituted $C_1$-$C_8$-alkoxycarbonyl group, substituted or non-substituted $C_1$-$C_8$-alkoxyamino group, substituted or non-substituted $C_2$-$C_8$-alkenyl, substituted or non-substituted $C_2$-$C_8$-alkynyl, substituted or non-substituted aryl-$C_2$-$C_8$-alkynyl, substituted or non-substituted $C_1$-$C_8$-alkylamino, substituted or non-substituted $C_3$-$C_{10}$-cycloalkylamino, or a group of formula QC(=U)$R^a$—

Even more preferred compounds of formula (I) according to the invention are those wherein $Z^1$ represents a halogen atom, a nitro group, a carboxylic acid, an amino group, substituted or non-substituted $C_2$-$C_8$-alkynyl, or a group of formula QC(=U)$NR^a$.

When $Z^1$ represents a group of formula QC(=U)$NR^a$, other preferred compounds of formula (I) according to the invention are those wherein U represents an oxygen atom.

When $Z^1$ represents a group of formula QC(=U)$NR^a$, other preferred compounds of formula (I) according to the invention are those wherein $R^a$ represents a hydrogen atom, a hydroxy group, substituted or non-substituted $C_1$-$C_8$-alkyl, substituted or non-substituted $C_3$-$C_8$-cycloalkyl, substituted or non-substituted $C_1$-$C_8$-alkoxy.

When $Z^1$ represents a group of formula QC(=U)$NR^a$, more preferred compounds of formula (I) according to the invention are those wherein $R^a$ represents a hydrogen atom.

When $Z^1$ represents a group of formula QC(=U)$NR^a$, other preferred compounds of formula (I) according to the invention are those wherein Q represents a substituted or non-substituted $C_1$-$C_8$-alkyl, substituted or non-substituted $C_3$-$C_8$-cycloalkyl, substituted or non-substituted $C_3$-$C_8$-cycloalkoxy, substituted or non-substituted $C_2$-$C_8$-alkynyl, substituted or non-substituted $C_2$-$C_3$-alkenyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylsulfenyl, substituted or non-substituted aryl, substituted or non-substituted heterocyclyl, substituted or non-substituted $C_3$-$C_8$-cycloalkyl-$C_1$-$C_8$-alkyl, substituted or non-substituted $C_3$-$C_8$-cycloalkyl-$C_1$-$C_8$-alkoxy, substituted or non-substituted $C_3$-$C_8$-cycloalkoxy-$C_1$-$C_8$-alkyl, substituted or non-substituted heterocyclyl-$C_1$-$C_8$-alkyl, substituted or non-substituted aryl-$C_1$-$C_8$-alkyl, substituted or non-substituted aryl-$C_1$-$C_8$-alkoxy, substituted or non-substituted aryloxy-$C_1$-$C_8$-alkyl, substituted or non-substituted $C_1$-$C_8$-alkoxy-$C_1$-$C_8$-alkyl;

When $Z^1$ represents a group of formula QC(=U)$NR^a$, more preferred compounds of formula (I) according to the invention are those wherein Q represents a substituted or non-substituted $C_4$-$C_3$-alkyl, substituted or non-substituted $C_3$-$C_8$-cycloalkyl, substituted or non-substituted $C_4$-$C_3$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl.

When $Z^1$ represents a group of formula QC(=U)$NR^a$, even more preferred compounds of formula (I) according to the invention are those wherein Q represents a substituted or non-substituted $C_4$-$C_8$-alkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted aryl, substituted or non-substituted heterocyclyl.

When $Z^1$ represents a group of formula QC(=U)$NR^a$, and when Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl, other preferred compounds of formula (I) according to the invention are those wherein substituents for Q are chosen in the list of a halogen atom, a cyano group, a (hydroxyimino)-$C_1$-$C_6$-alkyl group, a $C_1$-$C_8$-alkyl, $C_3$-$C_8$-cycloalkyl, a $C_2$-$C_8$-alkenyl, a $C_2$-$C_3$-alkynyl, a $C_2$-$C_8$-alkenyloxy, a $C_2$-$C_8$-alkynyloxy, a $C_1$-$C_8$-alkoxy, a $C_1$-$C_8$-alkylsulfenyl, a ($C_1$-$C_6$-alkoxyimino)-$C_1$-$C_8$-alkyl, a ($C_1$-$C_8$-alkenyloxyimino)-$C_1$-$C_8$-alkyl, a ($C_1$-$C_8$-alkynyloxyimino)-$C_1$-$C_6$-alkyl, (benzyloxyimino)-$C_1$-$C_6$-alkyl, $C_1$-$C_8$-alkoxyalkyl, benzyloxy, benzylsulfenyl, phenoxy, phenylsulfenyl, an aryl group or an heterocyclyl group, or wherein substituents form together a substituted or non-substituted, saturated or partially saturated 3-, 4-, 5-, 6-, 7-, 8-, 9-, 10-, or 11-membered cycle, which can be a carbocycle or a heterocycle comprising up to 4 heteroatoms selected from the list consisting of N, O, and S.

When $Z^1$ represents a group of formula QC(=U)$NR^a$, and when Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl, more preferred compounds of formula (I) according to the invention are those wherein substituents for Q are chosen in the list of a halogen atom, a cyano group, a (hydroxyimino)-$C_1$-$C_6$-alkyl group, a $C_1$-$C_8$-alkyl, $C_3$-$C_8$-cycloalkyl, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkoxy, a $C_1$-$C_8$-alkylsulfenyl, (benzyloxyimino)-$C_1$-$C_6$-alkyl, $C_1$-$C_8$-alkoxyalkyl, benzyloxy, phenoxy, an aryl group or an heterocyclyl group or wherein substituents form together a saturated or partially saturated 3-, 4-, 5-, 6-membered cycle, which can be a carbocycle or a heterocycle comprising up to 4 heteroatoms selected from the list consisting of N, O, and S.

Other preferred compounds of formula (I) according to the invention are those wherein $Z^2$, $Z^3$ and $Z^4$ independently represent a hydrogen atom, a halogen atom, substituted or non-substituted $C_1$-$C_8$-alkyl.

More preferred compounds of formula (I) according to the invention are those wherein $Z^2$, $Z^3$ and $Z^4$ independently represent a hydrogen atom.

Other preferred compounds of formula (I) according to the invention are those wherein $K^1$ represents a hydrogen atom, substituted or non-substituted $C_1$-$C_8$-alkyl.

More preferred compounds of formula (I) according to the invention are those wherein $K^1$ represents a methyl group.

Other preferred compounds of formula (I) according to the invention are those wherein $Y^1$ to $Y^5$ independently represent a hydrogen atom, a halogen atom, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-alkoxy.

More preferred compounds of formula (I) according to the invention are those wherein $Y^1$ to $Y^5$ independently represent a hydrogen atom, a halogen atom, methyl, ethyl, isopropyl, isobutyl, tertbutyl, trifluoromethyl, difluoromethyl, allyl, ethynyl, propargyl, cyclopropyl, methoxy or trifluoromethoxy.

Even more preferred compounds of formula (I) according to the invention are those wherein $Y^1$ to $Y^5$ independently represent a hydrogen atom or fluorine atom.

The above mentioned preferences with regard to the substituents of the compounds of formula (I) according to the invention can be combined in various manners. These combinations of preferred features thus provide sub-classes of compounds according to the invention. Examples of such sub-classes of preferred compounds according to the invention can combine:
- preferred features of A with preferred features of one or more of $X^1$ to $X^3$, $Y^1$ to $Y^5$;
- preferred features of $X^1$ with preferred features of one or more of A, $X^2$, $X^3$, Y1 to $Y^5$;
- preferred features of $X^2$ with preferred features of one or more of A, $X^1$, $X^3$, Y1 to $Y^5$;
- preferred features of $X^3$ with preferred features of one or more of A, $X^1$, $X^2$, Y1 to $Y^5$;
- preferred features of $Y^1$ with preferred features of one or more of A, $X^1$ to $X^3$, and $Y^2$ to $Y^5$;
- preferred features of $Y^2$ with preferred features of one or more of A, $X^1$ to $X^3$, $Y^1$ and $Y^3$ to $Y^5$;
- preferred features of $Y^3$ with preferred features of one or more of A, $X^1$ to $X^3$, $Y^1$ $Y^2$ $Y^4$ and $Y^5$;
- preferred features of $Y^4$ with preferred features of one or more of A, $X^1$ to $X^3$, $Y^1$ to $Y^3$ and $Y^5$;
- preferred features of $Y^5$ with preferred features of one or more of A, $X^1$ to $X^3$, and $Y^1$ to $Y^4$ In these combinations of preferred features of the substituents of the compounds according to the invention, the said preferred features can also be selected among the more preferred features of each of A, $X^1$ to $X^3$ and $Y^1$ to $Y^5$; so as to form most preferred subclasses of compounds according to the invention.

The present invention also relates to a process for the preparation of compounds of formula (I), Thus, according to a further aspect of the present invention, there is a provided a process P1 for the preparation of compounds of formula (Ia) from compounds of formula (II), by a reaction of nucleophilic substitution on compounds of formula (III) to yield to a compound of formula (IV), according to known methods, optionally in the presence of a base, according to known methods; followed by the addition of hydroxylamine or an hydroxylamine salt on compounds of formula (IV) to yield to a compound of formula (V), optionally in the presence of a base, optionally in the presence of an acid, according to known methods; followed by a reaction of cyclization of compounds of formula (V) to yield to a compound of formula (Ia), with a phosgene equivalent, optionally in the presence of a base, according to known methods; followed by a reaction of alkylation of compounds of formula (Ib) to yield to a compound of formula (Ia), with an alkylating agent of formula $X^1$-LGa, optionally in the presence of a base, according to known methods.

In such a case there is provided a process P1 according to the invention and such a process P1 can be illustrated by the following reaction scheme:

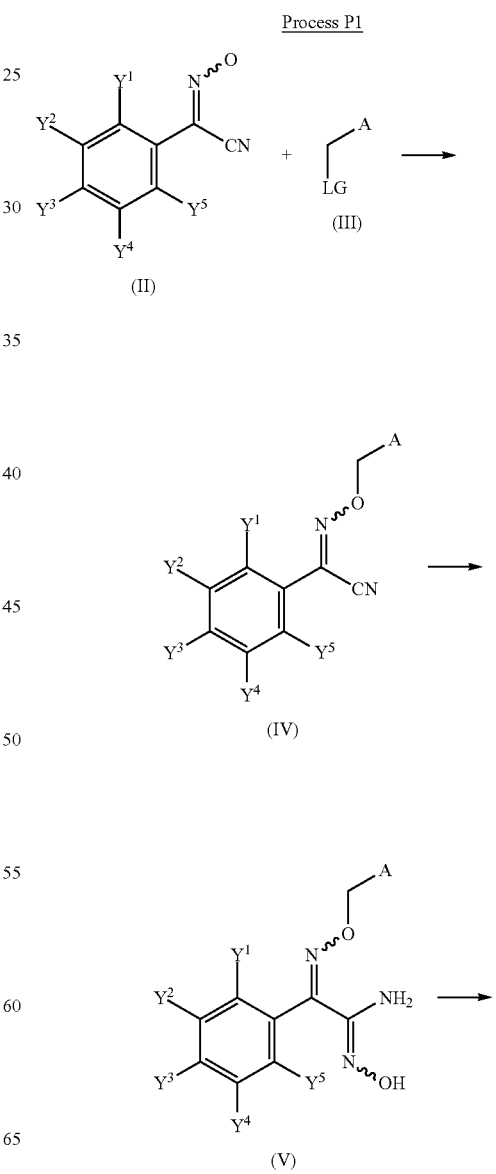

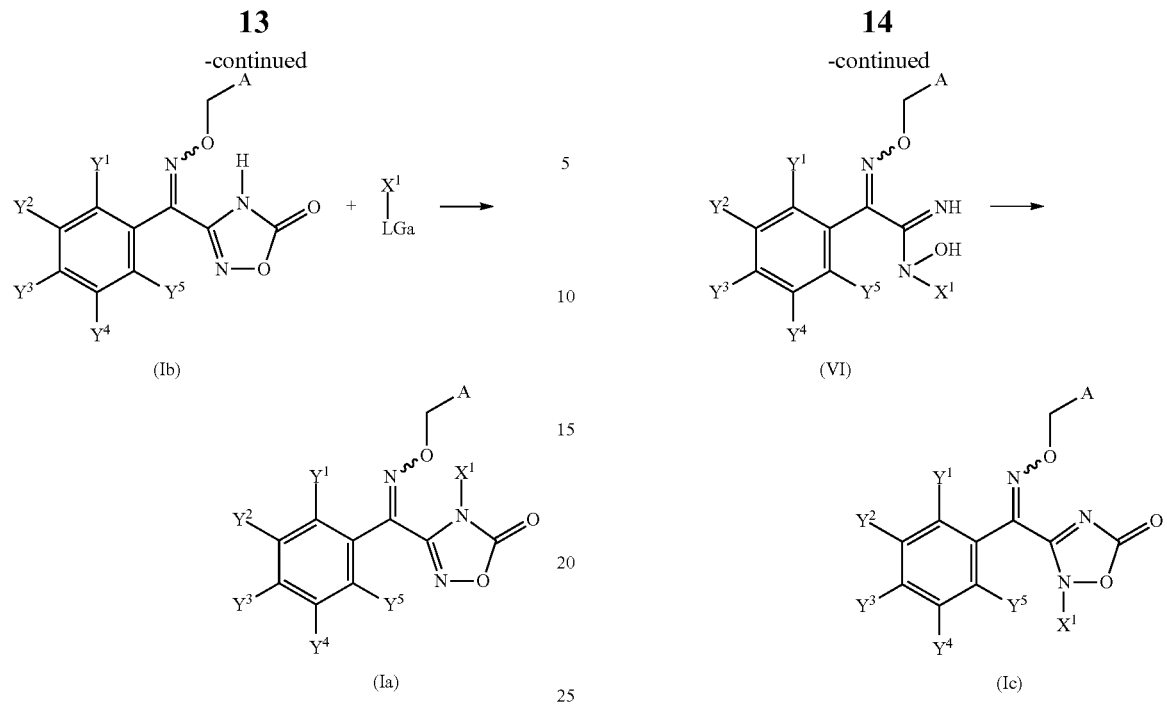

wherein $Y^1$, $Y^2$, $Y^3$, $Y^4$, $Y^5$, A and $X^1$ are as herein-defined and LG and LGa independently represent a leaving group. Suitable leaving groups can be selected in the list consisting of a halogen atom or other customary nucleofugal groups such as triflate, mesylate, or tosylate.

Suitable acids for the transformation of compounds of formula (IV) into compounds of formula (V) can be chosen as being a mineral acid such as hydrogen chloride and sulfuric acid, and an organic acid such as formic acid and acetic acid.

Suitable phosgene equivalent for the conversion of compounds of formula (V) into a compound of formula (I) can be chosen as being phosgene, diphosgene, triphosgene, carbonyl di-imidazole, a chlorformate derivative, such as ethyl chloroformate and 4-nitrophenoxy-chloroformate.

Compounds of formula (II) and (III) are commercially available or are easily accessible to the skilled worker in the art. Examples of preparation can be found in world patent application WO2009/130193. Compounds of formula $X^1$-LGa are commercially available.

In such a case there is provided a further process P2 according to the invention and such a process P2 can be illustrated by the following reaction scheme:

wherein $Y^1$, $Y^2$, $Y^3$, $Y^4$, $Y^5$, $X^1$ and A are as herein-defined.

Suitable phosgene equivalent for the conversion of compounds of formula (VI) into a compound of formula (I) can be chosen as being phosgene, diphosgene, triphosgene, carbonyl di-imidazole, a chlorformate derivative, such as ethyl chloroformate and 4-nitrophenoxy-chloroformate.

Hydroxylamine derivatives or an hydroxylamine derivative salts are commercially available or are easily accessible to the skilled worker in the art.

According to the invention, there is provided a further process P3 for the preparation of compounds of formula (Ie) from compounds of formula (Id).

For the compounds of formula (Id) according to the invention if $Z^1$ represents represent —$NHR^a$, process P1 or P2 according to the invention can be completed by a further step comprising the additional modification of this group, notably by a reaction of acylation, alkoxycarbonylation, alkylaminocarbonylation, (thio)acylation, alkoxy(thio)carbonylation, alkylsuphenyl(thio)carbonylation or alkylamino(thio)carbonylation to yield to a compound of formula (Ie), according to known methods. In such a case there is provided a process P3 according to the invention and such a process P3 can be illustrated by the following reaction scheme:

Process P2

Process P3

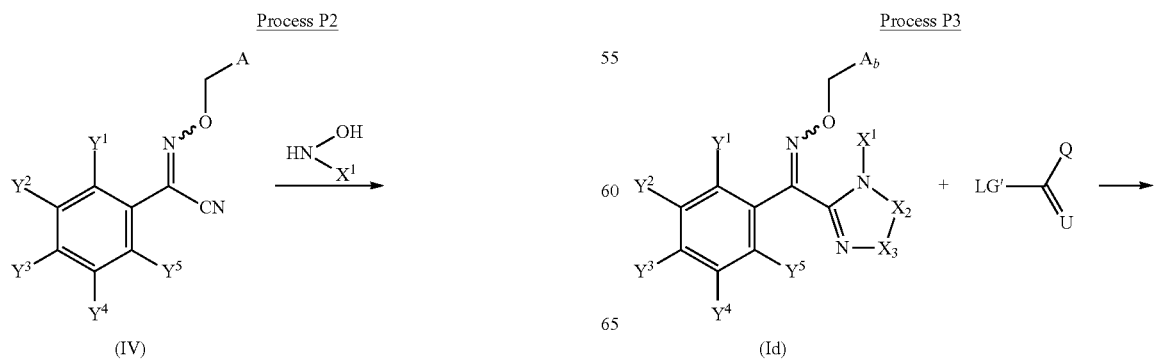

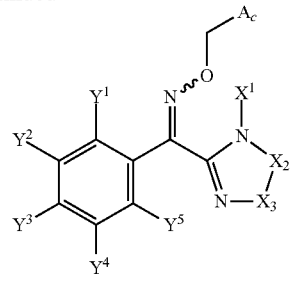

(Ie)

Wherein
$Y^1$, $Y^2$, $Y^3$, $Y^4$, $Y^5$, $X^1$, $X^2$, $X^3$, U, $R^a$ and Q are as herein-defined and $A_b$ represents A wherein $Z^1$ represents —$NHR^a$; $A_c$ represents A wherein $Z^1$ represents a group of formula QC(=U)$NR^a$ and LG' represents a leaving group.

Suitable leaving groups can be selected in the list consisting of a halogen atom or other customary nucleofugal groups such as alcoolate, hydroxide or cyanide.

According to the invention, there is provided a further process P4 for the preparation of compounds of formula (Ig) from compounds of formula (If), by a reaction of nucleophilic substitution to yield to a compound of formula (Ig), according to known methods, optionally in the presence of a catalyst notably a transition metal catalyst, such as palladium salts or complexes for example palladium (II) chloride, palladium (II) acetate, tetrakis-(triphenylphosphine) palladium(0), bis-(triphenylphosphine) palladium dichloride (II), tris(dibenzylideneacetone) dipalladium(0), bis(dibenzylideneacetone) palladium(0) or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino) benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butyl-phenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl] ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine, optionally in the presence of a base such as an inorganic or an organic base; preferably an alkaline earth metal or alkali metal hydride, hydroxide, amide, alcoholate, acetate, carbonate or hydrogen carbonate, such as sodium hydride, sodium amide, lithiium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), according to known methods. In such a case there is provided a process P4 according to the invention and such a process P4 can be illustrated by the following reaction scheme:

Process P4

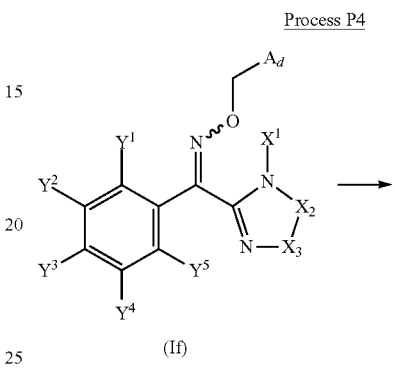

(If)

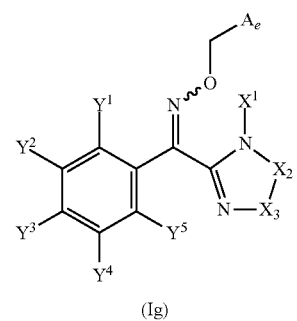

(Ig)

wherein
$Y^1$, $Y^2$, $Y^3$, $Y^4$, $Y^5$, $X^1$, $X^2$ and $X^3$ are as herein-defined and $A_d$ represents A wherein $Z^1$ represents a halogen atom; $A_e$ represents A wherein $Z^1$ represents a hydroxy group, a cyano group, a sulfenyl group, a formyloxy group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkyl, substituted or non-substituted $C_3$-$C_8$-cycloalkyl, a $C_2$-$C_8$-alkenyl, substituted or non-substituted $C_2$-$C_8$-alkynyl, substituted or non-substituted $C_1$-$C_3$-alkoxy, substituted or non-substituted $C_2$-$C_8$-alkenyloxy, substituted or non-substituted $C_3$-$C_8$-alkynyloxy, substituted or non-substituted $C_1$-$C_8$-alkylcarbonyloxy, substituted or non-substituted N—$C_1$-$C_8$-alkylaminocarbonyloxy, substituted or non-substituted N,N'-di-$C_1$-$C_8$-alkylaminocarbonyloxy, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_1$-$C_8$-alkylsulfinyl, substituted or non-substituted phenoxy, substituted or non-substituted phenylsulfenyl, substituted or non-substituted aryl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula QC(=O)NHR$^a$.

According to the invention, there is provided a further process P5 for the preparation of compounds of formula (Ii) from compounds of formula (Ih).

For the compounds of formula (Ih) according to the invention, $A_f$ represents A wherein $Z^1$ represents a group of formula QC(=O)NR$^a$, process P1 or P2 according to the invention can be completed by a further step comprising the additional modification of this group, notably by a reaction of thiocarbonylation in the presence of a thiocarbonylating agent such as 2,4-bis(4-methoxyphenyl)-1,3,2,4-dithiadiphosphetane 2,4-disulfide, phosphorus pentasulfide, sulfur to yield to a compound of formula (Ii), according to known methods. In such a case there is provided a process P5 according to the invention and such a process P5 can be illustrated by the following reaction scheme:

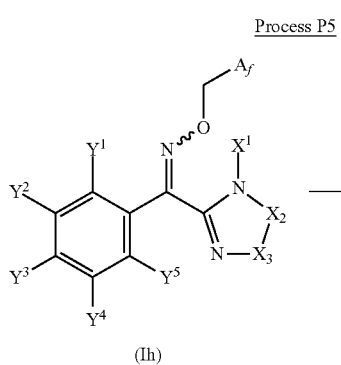

Wherein
$Y^1$, $Y^2$, $Y^3$, $Y^4$, $Y^5$, $X^1$, $X^2$, $X^3$, R$^a$ and Q are as herein-defined;
$A_f$ represents A wherein $Z^1$ represents a group of formula QC(=O)NR$^a$
and $A_g$ represents A wherein $Z^1$ represents a group of formula QC(=S)NR$^a$.

The present invention also relates to a process for the preparation of compounds of formula (Ia), Thus, according to a further aspect of the present invention, there is provided a process P6 for the preparation of compounds of formula (Ia) from compounds of formula (VII), by a reaction of oxidation compounds of formula (VII) in a presence of a suitable oxidizing agent to yield to a compound of compounds of formula (VIII), followed by a condensation of compounds of formula (IX), optionally under microwave irradiation, optionally in the presence of a dehydrating agent, such as molecular sieves, to yield to compounds of formula (Ia), according to known methods. In such a case there is provided a process P6, according to the invention and such a process P6 can be illustrated by the following reaction scheme:

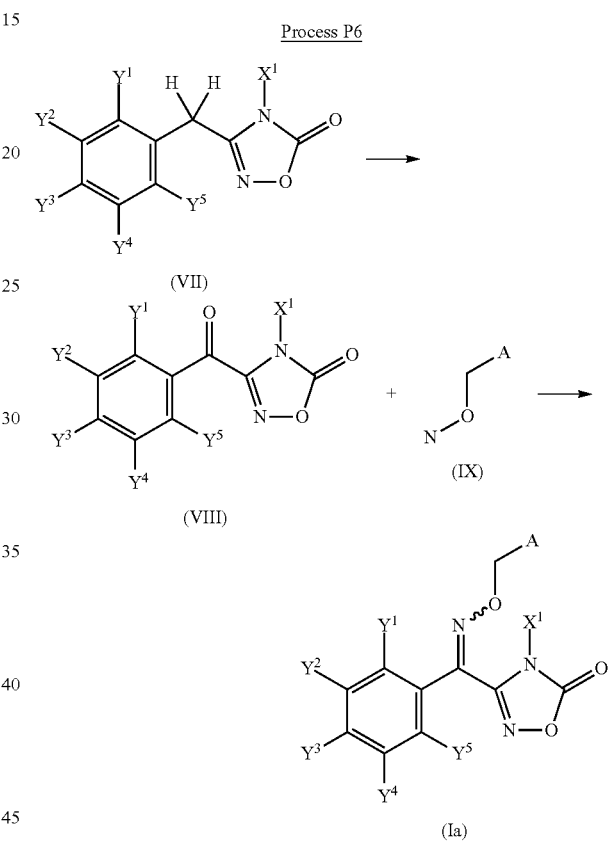

wherein $Y^1$, $Y^2$, $Y^3$, $Y^4$, $Y^5$, A and $X^1$ areas herein-defined.

Examples of oxidations at the methylene position between a phenyl ring and an heterocycle to yield an oxo substituent are known and can be found for example in Journal of the Chemical Society, Perkin Transactions 1: Organic and Bio-Organic Chemistry (1972-1999) (1982), (12), 2995-3006. Suitable oxidizing agents for carrying out the first step of process P5 according to the invention can be inorganic and organic peroxides such as hydrogen peroxide and benzoyl peroxide, metallic and metalloïdic oxides such as manganese (IV) oxide, chromium (VI) oxide, oxygen optionally in the presence of singlet oxygen activator, halogenating agents in an aqueous medium such as bleach.

Compounds of formula (VII) are easily accessible to the skilled worker in the art. Examples of preparation can be found in Annali di Chimica (Rome, Italy), (1963), 53(10), 1405-10

Examples of condensations of compounds of formula (VIII) with compounds of formula (IX) can be found in world patent application WO2010/000841.

Compounds of formula (IX) are easily accessible to the skilled worker in the art. Examples of preparation can be found in world patent application WO2010/000841.

According to the invention, there is provided a further process P7 for the preparation of compounds of formula (Ii) from compounds of formula (Ih), by a reaction of alkylation, according to known methods. In such a case there is provided a process P6 according to the invention and such a process P6 can be illustrated by the following reaction scheme:

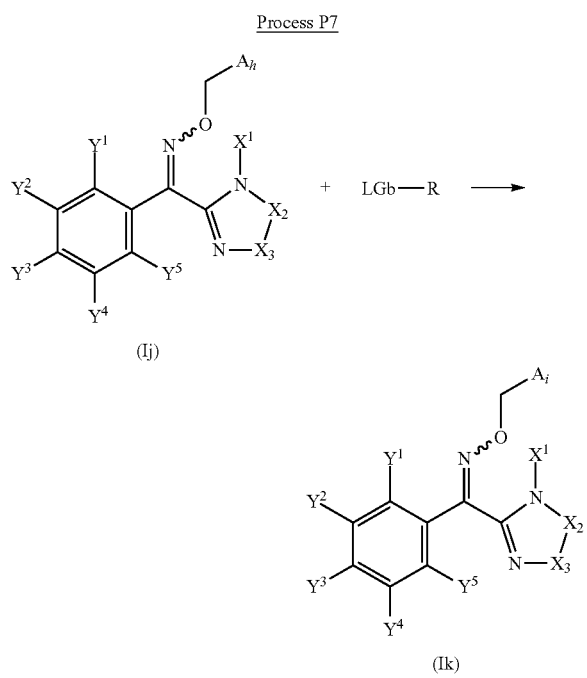

(Ik)

Wherein $Y^1$, $Y^2$, $Y^3$, $Y^4$, $Y^5$, $X^1$, $X^2$ and $X^3$ are as herein-defined $A_h$ represents A wherein $Z^1$ represents an amino, substituted or non-substituted $C_1$-$C_8$-alkylamino or a group of formula —NHC(=O)Q wherein Q is as herein defined $A_i$ represents A wherein $Z^1$ represents substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted heterocyclylamino, or a group of formula QC(=U)NR R represents optionally substituted $C_1$-$C_8$-alkyl, $C_2$-$C_8$-alkenyl, $C_2$-$C_8$-alkynyl, $C_3$-$C_{10}$-cycloalkyl, $C_3$-$C_{10}$-cycloalkenyl, $C_3$-$C_{10}$-fused bicycloalkyl, $C_5$-$C_{12}$-fused bicycloalkenyl $LG_b$ represents a leaving group.

Suitable leaving groups can be selected in the list consisting of a halogen atom or other customary nucleofugal groups such as alcoolate, hydroxide or cyanide.

According to the invention, there is provided a further process P8 for the preparation of compounds of formula (Im) from compounds of formula (II), by a reaction of deprotection, according to known methods. In such a case there is provided a process P8 according to the invention and such a process P8 can be illustrated by the following reaction scheme:

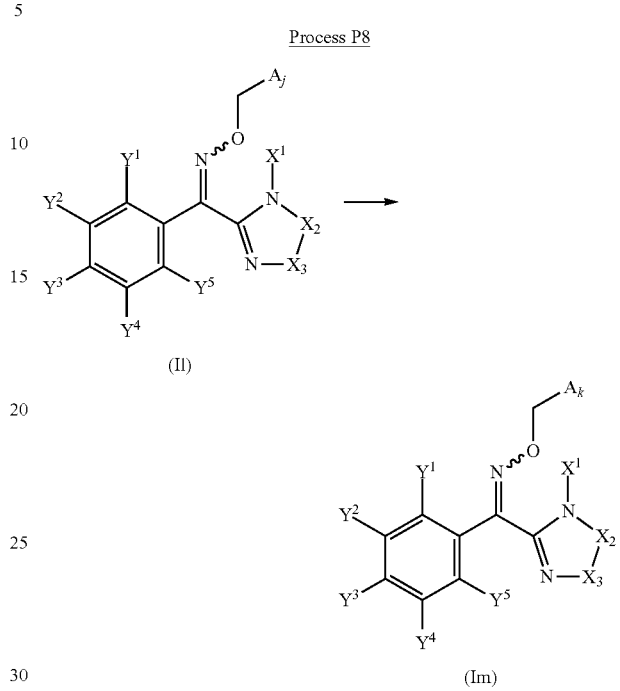

Wherein $Y^1$, $Y^2$, $Y^3$, $Y^4$, $Y^5$, $X^1$, $X^2$ and $X^3$ are as herein-defined $A_j$ represents A wherein $Z^1$ represents a group of formula $Z^1_a$-PG wherein $Z^1_a$ represents a substituted or non-substituted $C_1$-$C_8$-alkoxyamino, substituted or non-substituted $C_1$-$C_8$-alkylamino, a substituted or non-substituted $C_2$-$C_8$-alkenylamino, substituted or non-substituted $C_2$-$C_8$-alkynylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_3$-alkylamino, substituted or non-substituted phenylamino, substituted or non-substituted heterocyclylamino and PG represents a protecting group such as a formyl group, $C_1$-$C_8$-alkylcarbonyl, $C_1$-$C_8$-alkoxycarbonyl, $C_1$-$C_8$-alkoxy-$C_1$-$C_2$-alkyl, tri($C_1$-$C_8$-alkyl)silyl $C_1$-$C_2$-alkyl, tri($C_1$-$C_8$-alkyl)silyloxy-$C_1$-$C_2$-alkyl;

$A_k$ represents A wherein $Z^1$ represents $Z^1_a$;

Amino-protecting groups and related methods of cleavage thereof are known and can be found in T. W. Greene and P. G. M. Wuts, *Protective Group in Organic Chemistry*, 3$^{rd}$ ed., John Wiley & Sons.

According to the invention, there is provided a further process P9 for the preparation of compounds of formula (Io) from compounds of formula (In), by a reaction of aminoreduction, in the presence of a reducing agent, such as hydrogen gas or an hydride derivative, in particular sodium cyanoborohydride, according to known methods. In such a case there is provided a process P9 according to the invention and such a process P9 can be illustrated by the following reaction scheme:

Process P9

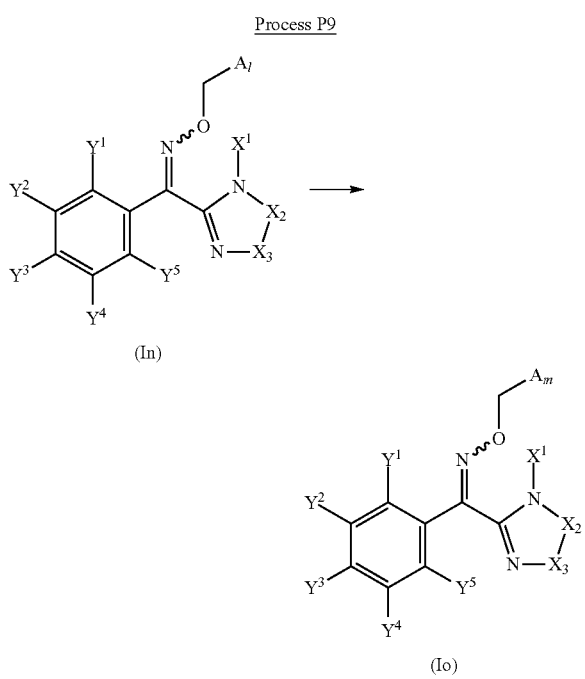

Wherein
Y$^1$, Y$^2$, Y$^3$, Y$^4$, Y$^5$, X$^1$, X$^2$ and X$^3$ are as herein-defined;
A$_l$ represents A wherein Z$^1$ represents an amino group, a substituted or non-substituted C$_1$-C$_8$-alkylamino;
A$_m$ represents A wherein Z$^1$ represents a substituted or non-substituted C$_1$-C$_8$-alkylamino, substituted or non-substituted di-C$_1$-C$_8$-alkylamino.

According to the invention, there is provided a further process P10 for the preparation of compounds of formula (Iq) from compounds of formula (Ip) according to the following reaction scheme in either one or two steps.

Process P10

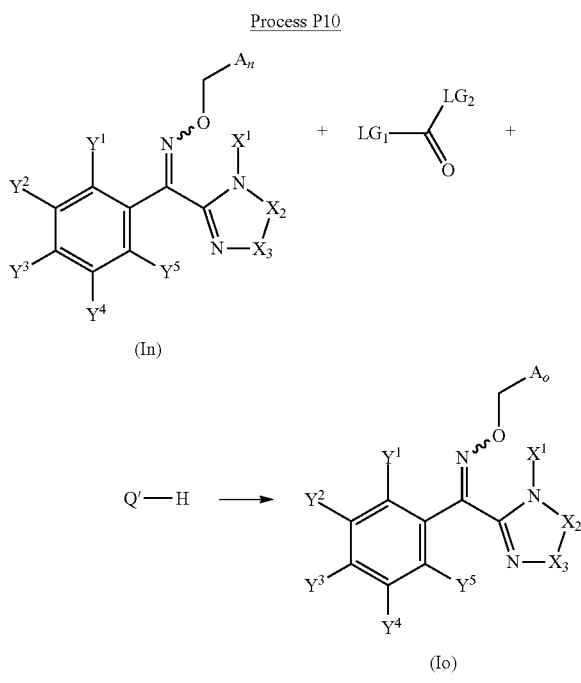

Wherein
Y$^1$, Y$^2$, Y$^3$, Y$^4$, Y$^5$, X$^1$, X$^2$ and X$^3$, R$^a$ are as herein-defined;
A$_n$ represents A wherein Z$^1$ represents —NHR$^a$;
A$_o$ represents A wherein Z$^1$ represents Q'C(=O)NR$^a$ wherein Q' represents substituted or non-substituted C$_1$-C$_8$-alkoxy, substituted or non-substituted C$_2$-C$_8$-alkenyloxy, substituted or non-substituted C$_2$-C$_8$-alkynyloxy, substituted or non-substituted C$_1$-C$_8$-alkylsulfenyl, substituted or non-substituted C$_2$-C$_8$-alkenylsulfenyl, substituted or non-substituted C$_2$-C$_8$-alkynylsulfenyl, substituted or non-substituted arylsulfenyl, substituted or non-substituted cycloalkoxy; substituted or non-substituted cycloalkenyloxy, substituted or non-substituted aryloxy; substituted or non-substituted heterocyclyloxy, substituted or non-substituted C$_5$-C$_{12}$-fused bicycloalkoxy, substituted or non-substituted C$_5$-C$_{12}$-fused bicycloalkenyloxy, substituted or non-substituted C$_5$-C$_{12}$-benzofused carbocyclyloxy, or non-substituted C$_5$-C$_{12}$-benzofused heterocyclyloxy;
LG$_1$ and LG$_2$ represent leaving groups
Suitable leaving groups can be selected in the list consisting of a halogen atom or other customary nucleofugal groups such as imidazole, halogenophenoxide or the likes.

According to the invention, processes P1 to P10 can be performed if appropriate in the presence of a solvent and if appropriate in the presence of a base.

According to the invention, process P3 can be performed if appropriate in the presence of a catalyst. Suitable catalyst can be chosen as being 4-dimethyl-aminopyridine, 1-hydroxy-benzotriazole or dimethylformamide.

In case LG' represents a hydroxy group, the process P3 according to the present invention can be performed in the presence of condensing agent. Suitable condensing agent can be chosen as being acid halide former, such as phosgene, phosphorous tri-bro-mide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy [1.3.5]triazin-2-yl)-4-methylmorpholinium chloride hydrate or bromo-tripyrrolidino-phosphonium-hexafluorophosphate.

Suitable solvents for carrying out processes P1 to P10 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulfoxides, such as dimethyl sulfoxide or sulfones, such as sulfolane.

Suitable bases for carrying out processes P1 to P10 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diaza-bicyclo[5.4.0]undec-7-ene (DBU).

If carrying out processes P1 to P10, according to the invention, the reaction temperature can independently be varied within a relatively wide range. Generally, process P1 according to the invention is carried out at temperatures between −20° C. and 160° C.

Processes P1 to P10 according to the invention are generally independently carried out under atmospheric pressure. However, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that can still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesised.

When A is $A^1$, as herein described, the compounds of formula (IV) can be advantageously prepared according to the method described in WO2011/080254, hereby incorporated by reference.

In a further aspect, if A is selected in the list consisting of $A^2$ to $A^{25}$, as herein-described, the present invention relates to compounds of formula (IV) useful as intermediate compounds or materials for the process of preparation according to the invention.

The present invention thus provides compounds of formula (IV) wherein $Y^1$, $Y^2$, $Y^3$, $Y^4$ and $Y^5$ are as herein-defined and A is selected in the list consisting of $A^2$ to $A^{25}$.

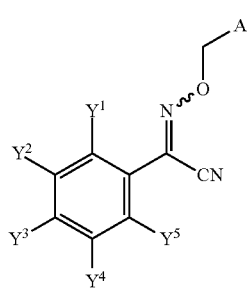

(IV)

In a further aspect, the present invention relates to compounds of formula (V) useful as intermediate compounds or materials for the process of preparation according to the invention.

The present invention thus provides compounds of formula (V) wherein $Y^1$, $Y^2$, $Y^3$, $Y^4$, $Y^5$ and A are as herein-defined.

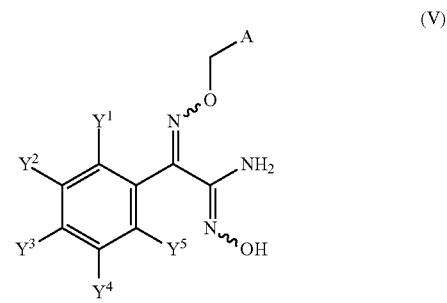

(V)

In a further aspect, the present invention relates to compounds of formula (VI) useful as intermediate compounds or materials for the process of preparation according to the invention.

The present invention thus provides compounds of formula (VI) wherein $Y^1$, $Y^2$, $Y^3$, $Y^4$, $Y^5$, $X^1$ and A are as herein-defined.

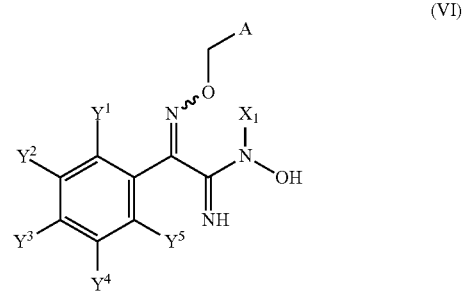

(VI)

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic organic or inorganic compound with which the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyols and derivatives of the above compounds containing sulfate, sulfonate and phosphate functions. The presence of at least one surfactant is generally essential if the active compound and/or the inert support are water-insoluble and if the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous. The composition according to the invention comprising a mixture of a compound of formula (I) with a bactericide compound can also be particularly advantageous.

According to another object of the present invention, there is provided a method for controlling the phytopathogenic fungi of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow.

The expression "are applied to the plants to be treated" is understood to mean, for the purposes of the present invention, that the pesticide composition which is the subject of the invention can be applied by means of various methods of treatment such as:
  spraying onto the aerial parts of the said plants a liquid comprising one of the said compositions,
  dusting, the incorporation into the soil of granules or powders, spraying, around the said plants and in the case of trees injection or daubing,
  coating or film-coating the seeds of the said plants with the aid of a plant-protection mixture comprising one of the said compositions.

The method according to the invention can either be a curing, preventing or eradicating method. In this method, a composition used can be prepared beforehand by mixing the two or more active compounds according to the invention.

According to an alternative of such a method, it is also possible to apply simultaneously, successively or separately compounds (A) and (B) so as to have the conjugated (A)/(B) effects, of distinct compositions each containing one of the two or three active ingredients (A) or (B).

The dose of active compound usually applied in the method of treatment according to the invention is generally and advantageously
  for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;
  for seed treatment: from 2 to 200 g per 100 kilogram of seed, preferably from 3 to 150 g per 100 kilogram of seed;
  for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or controlled, a lower dose can offer adequate protection. Certain climatic conditions, resistance or other factors like the nature of the phytopathogenic fungi or the degree of infestation, for example, of the plants with these fungi, can require higher doses of combined active ingredients. The optimum dose usually depends on several factors, for example on the type of phytopathogenic fungus to be treated, on the type or level of development of the infested plant, on the density of vegetation or alternatively on the method of application.

Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant. Among the plants that can be protected by the method according to the invention, mention can be made of cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantins), Rubiaceae sp., Theaceae sp., Sterculiceae sp., Rutaceae sp. (for instance lemons oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots); horticultural and forest crops; as well as genetically modified homologues of these crops.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a *Petunia* EPSPS, a Tomato EPSPS, or an *Eleusine* EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226. Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in U.S. Pat. No. 5,605,011, U.S. Pat. No. 5,378,824, U.S. Pat. No. 5,141,870, and U.S. Pat. No. 5,013,659. The production of sulfonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 1997/41218, for sugar beet in U.S.

Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance. An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose) polymerase (PARP) gene in the plant cells or plants as described in WO 2000/004173 or WO2006/045633 or b. plants which contain a stress tolerance enhancing transgene capable of reducing the expression and/or the activity of the PARG encoding genes of the plants or plants cells, as described e.g. in WO 2004/090140.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO99/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026, WO 1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
  a) Plants, such as cotton plants, containing an altered form of cellulose synthase genes as described in WO 1998/000549
  b) Plants, such as cotton plants, containing an altered form of rsw2 or rsw3 homologous nucleic acids as described in WO2004/053219
  c) Plants, such as cotton plants, with increased expression of sucrose phosphate synthase as described in WO 2001/017333
  d) Plants, such as cotton plants, with increased expression of sucrose synthase as described in WO02/45485
  e) Plants, such as cotton plants, wherein the timing of the plasmodesmatal gating at the basis of the fiber cell is altered, e.g. through downregulation of fiberselective β 1,3-glucanase as described in WO2005/017157
  f) Plants, such as cotton plants, having fibers with altered reactivity, e.g. through the expression of N-acteylglucosaminetransferase gene including nodC and chitinsynthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:
  a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
  b) Plants such as oilseed rape plants, producing oil having a low linolenic acid content as described in U.S. Pat. No. 6,270,828, U.S. Pat. No. 6,169,190 or U.S. Pat. No. 5,965,755
  c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B®(cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned include the varieties sold under the name Clearfield® (for example maize).

The composition according to the invention can also be used against fungal diseases liable to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, spraying, dipping, injection or any other suitable means.

Among the diseases of plants or crops that can be controlled by the method according to the invention, mention can be made of:
Powdery mildew diseases such as:
  *Blumeria* diseases, caused for example by *Blumeria graminis*;
  *Podosphaera* diseases, caused for example by *Podosphaera leucotricha*;
  *Sphaerotheca* diseases, caused for example by *Sphaerotheca fuliginea*;
  *Uncinula* diseases, caused for example by *Uncinula necator*;
Rust diseases such as:
  *Gymnosporangium* diseases, caused for example by *Gymnosporangium sabinae*;
  *Hemileia* diseases, caused for example by *Hemileia vastatrix*;
  *Phakopsora* Diseases, Caused for Example by *Phakopsora pachyrhizi* or *Phakopsora meibomiae*;
  *Puccinia* diseases, caused for example by *Puccinia recondita*;
  *Uromyces* diseases, caused for example by *Uromyces appendiculatus*;
Oomycete diseases such as:
  *Bremia* diseases, caused for example by *Bremia lactucae*;
  *Peronospora* diseases, caused for example by *Peronospora pisi* or *P. brassicae*;
  *Phytophthora* diseases, caused for example by *Phytophthora infestans*;
  *Plasmopara* diseases, caused for example by *Plasmopara viticola*;

*Pseudoperonospora* diseases, caused for example by *Pseudoperonospora humuli* or *Pseudoperonospora cubensis*;
*Pythium* diseases, caused for example by *Pythium ultimum*;
Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporium cucumerinum*;
*Cochliobolus* diseases, caused for example by *Cochliobolus sativus*;
*Colletotrichum* diseases, caused for example by *Colletotrichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans*; *Leptosphaeria nodorum*;
*Magnaporthe* diseases, caused for example by *Magnaporthe grisea*;
*Mycosphaerella* diseases, caused for example by *Mycosphaerella graminicola*; *Mycosphaerella arachidicola*; *Mycosphaerella fijiensis*;
*Phaeosphaeria* diseases, caused for example by *Phaeosphaeria nodorum*;
*Pyrenophora* diseases, caused for example by *Pyrenophora teres*;
*Ramularia* diseases, caused for example by *Ramularia collo-cygni*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incarnate*;
*Venturia* diseases, caused for example by *Venturia inaequalis*;
Root and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Tapesia* diseases, caused for example by *Tapesia acuformis*;
*Thielaviopsis* diseases, caused for example by *Thielaviopsis basicola*;
Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;
Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;
Fruit rot and mould diseases such as:
*Aspergillus* diseases, caused for example by *Aspergillus flavus*;
*Botrytis* diseases, caused for example by *Botrytis cinerea*;
*Penicillium* diseases, caused for example by *Penicillium expansum*;
*Sclerotinia* diseases, caused for example by *Sclerotinia sclerotiorum*;
*Verticilium* diseases, caused for example by *Verticilium alboatrum*;
Seed and soilborne decay, mould, wilt, rot and damping-off diseases:
*Alternaria* diseases, caused for example by *Alternaria brassicicola*
*Aphanomyces* diseases, caused for example by *Aphanomyces euteiches*
*Ascochyta* diseases, caused for example by *Ascochyta lentis*
*Aspergillus* diseases, caused for example by *Aspergillus flavus*
*Cladosporium* diseases, caused for example by *Cladosporium herbarum*
*Cochliobolus* diseases, caused for example by *Cochliobolus sativus*
(Conidiaform: *Drechslera*, *Bipolaris* Syn: *Helminthosporium*);
*Colletotrichum* diseases, caused for example by *Colletotrichum coccodes*;
*Fusarium* diseases, caused for example by *Fusarium culmorum*;
*Gibberella* diseases, caused for example by *Gibberella zeae*;
*Macrophomina* diseases, caused for example by *Macrophomina phaseolina*
*Monographella* diseases, caused for example by *Monographella nivalis*;
*Penicillium* diseases, caused for example by *Penicillium expansum*
*Phoma* diseases, caused for example by *Phoma lingam*
*Phomopsis* diseases, caused for example by *Phomopsis sojae*;
*Phytophthora* diseases, caused for example by *Phytophthora cactorum*;
*Pyrenophora* diseases, caused for example by *Pyrenophora graminea*
*Pyricularia* diseases, caused for example by *Pyricularia oryzae*;
*Pythium* diseases, caused for example by *Pythium ultimum*;

Rhizoctonia diseases, caused for example by *Rhizoctonia solani*;
Rhizopus diseases, caused for example by *Rhizopus oryzae*
Sclerotium diseases, caused for example by *Sclerotium rolfsii*;
Septoria diseases, caused for example by *Septoria nodorum*;
Typhula diseases, caused for example by *Typhula incarnate*;
Verticillium diseases, caused for example by *Verticillium dahliae*;
Canker, broom and dieback diseases such as:
Nectria diseases, caused for example by *Nectria galligena*;
Blight diseases such as:
Monilinia diseases, caused for example by *Monilinia laxa*;
Leaf blister or leaf curl diseases such as:
Taphrina diseases, caused for example by *Taphrina deformans*;
Decline diseases of wooden plants such as:
Esca diseases, caused for example by *Phaemoniella clamydospora*;
Eutypa dyeback, caused for example by *Eutypa lata*;
Dutch elm disease, caused for example by *Ceratocystsc ulmi*;
Diseases of flowers and Seeds such as:
Botrytis diseases, caused for example by *Botrytis cinerea*;
Diseases of tubers such as:
Rhizoctonia diseases, caused for example by *Rhizoctonia solani*
Helminthosporium diseases, caused for example by *Helminthosporium solani*.

The compounds according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The present invention further relates to the use of compounds of the formula (I) as herein defined for the control of phytopathogenic fungi.

The present invention further relates to the use of compounds of the formula (I) as herein defined for the treatment of transgenic plants.

The present invention further relates to the use of compounds of the formula (I) as herein defined for the treatment of seed and of seed of transgenic plants.

The present invention further relates to a process for producing compositions for controlling phytopathogenic harmful fungi, characterized in that derivatives of the formula (I) as herein defined are mixed with extenders and/or surfactants.

The various aspects of the invention will now be illustrated with reference to the following table 1 of compound examples and the following preparation or efficacy examples.

The various aspects of the invention will now be illustrated with reference to the following Table 1 of compound examples and the following preparation or efficacy examples.

The following Table 1 illustrates in a non-limiting manner examples of compounds according to the invention.

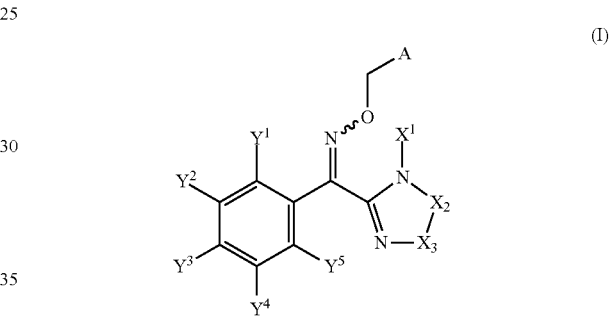

In table 1, we use this following abbreviation for specified claimed elements $A^1$, $A^{14}$ of the generic structure (I) of the invention:

TABLE 1

$A^1$

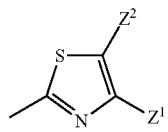

$A^{14}$

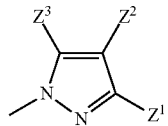

| ID | Y1 | Y2 | Y3 | Y4 | Y5 | X1 | X2 | X3 | A | Z1 | Z2 | Z3 | Stereo-chemistry | LogP |
|----|----|----|----|----|----|----|----|----|----|----|----|----|-----|------|
| 1 | H | H | H | H | H | Me | CO | O | A1 | [(but-3-yn-1-yloxy)carbonyl]amino | H | | Z | 2.97[a] |
| 2 | H | H | H | H | H | Me | O | CO | A14 | NO2 | H | H | Z | 2.10[a] |
| 3 | H | H | H | H | H | Me | CO | O | A1 | Br | H | | Z | 3.25[a] |
| 4 | H | H | H | H | H | Me | O | CO | A1 | cyclopropylethynyl | H | | Z | 3.04[a] |
| 5 | H | H | H | H | H | Me | CO | O | A1 | tert-butylcarbamoyl | H | | Z | 3.22[a] |
| 6 | H | H | H | H | H | Me | CO | O | A1 | (tert-butoxycarbonyl)amino | H | | Z | 3.64[a] |

TABLE 1-continued

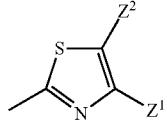

A¹

A¹⁴

| ID | Y1 | Y2 | Y3 | Y4 | Y5 | X1 | X2 | X3 | A | Z1 | Z2 | Z3 | Stereo-chemistry | LogP |
|---|---|---|---|---|---|---|---|---|---|---|---|---|---|---|
| 7  | H | H | H | H | H | Me | O  | CO | A14 | [(pentyloxy)carbonyl]amino | H | H | Z | 3.06[a] |
| 8  | H | H | H | H | H | Me | O  | CO | A14 | NH2 | H | H | Z | 1.29[a] |
| 9  | H | H | H | H | H | Me | CO | O  | A1 | cyclohexylcarbamoyl | H |   | Z | 3.43[a] |
| 10 | H | H | H | H | H | Me | CO | O  | A1 | cyclopropylethynyl | H |   | Z | 3.56[a] |
| 11 | H | H | H | H | H | Me | CO | O  | A1 | (2,2-dimethylpropanoyl)amino | H |   | Z | 3.23[a] |
| 12 | H | H | H | H | H | Me | CO | O  | A1 | 4-phenylbut-1-yn-1-yl | H |   | Z | 4.30[a] |
| 13 | H | H | H | H | H | Me | CO | O  | A1 | (4-fluorophenyl)ethynyl | H |   | Z | 4.09[a] |
| 14 | H | H | H | H | H | Me | O  | CO | A1 | Br | H |   | Z | 2.60[a] |
| 15 | H | H | H | H | H | Me | CO | O  | A1 | (2-phenylethyl)carbamoyl | H |   | Z | 3.27[a] |
| 16 | H | H | H | H | H | Me | CO | O  | A1 | phenylcarbamoyl | H |   | Z | 3.29[a] |
| 17 | H | H | H | H | H | Me | CO | O  | A1 | (4-methylbenzoyl)amino | H |   | Z | 3.34[a] |
| 18 | H | H | H | H | H | Me | CO | O  | A1 | hexylcarbamoyl | H |   | Z | 3.76[a] |
| 19 | H | H | H | H | H | Me | CO | O  | A1 | (phenylacetyl)amino | H |   | Z | 3.21[a] |
| 20 | H | H | H | H | H | Me | CO | O  | A1 | 5-phenylpent-1-yn-1-yl | H |   | Z | 4.68[a] |
| 21 | H | H | H | H | H | Me | CO | O  | A1 | hex-1-yn-1-yl | H |   | Z | 4.26[a] |
| 22 | H | H | H | H | H | Me | CO | O  | A1 | pent-1-yn-1-yl | H |   | Z | 3.87[a] |
| 23 | H | H | H | H | H | Me | CO | O  | A1 | 3-methylbut-1-yn-1-yl | H |   | Z | 3.86[a] |
| 24 | H | H | H | H | H | Me | CO | O  | A1 | (1E)-hex-1-en-1-yl | H |   | Z | 4.77[a] |
| 25 | H | H | H | H | H | H  | CO | O  | A1 | hex-1-yn-1-yl | H |   | Z | 3.39[a] |
| 26 | H | H | H | H | H | H  | CO | O  | A1 | pent-1-yn-1-yl | H |   | Z | 3.47[a] |
| 27 | H | H | H | H | H | Me | CO | O  | A1 | (3,4-dihydro-2H-chromen-2-ylcarbonyl)amino | H |   | Z | 3.77[a] |
| 28 | H | H | H | H | H | Me | CO | O  | A1 | (phenoxyacetyl)amino | H |   | Z | 3.30[a] |
| 29 | H | H | H | H | H | Me | CO | O  | A1 | (E)-2-cyclohexylvinyl | H |   | Z | 5.39[a] |
| 30 | H | H | H | H | H | Me | CO | O  | A1 | (1E)-hept-1-en-1-yl | H |   | Z | 5.23[a] |
| 31 | H | H | H | H | H | Me | CO | O  | A1 | cyclohexylethynyl | H |   | Z | 4.80[a] |
| 32 | H | H | H | H | H | H  | CO | O  | A1 | cyclohexylethynyl | H |   | Z | 4.33[a] |
| 33 | H | H | H | H | H | H  | CO | O  | A1 | hept-1-yn-1-yl | H |   | Z | 4.26[a] |
| 34 | H | H | H | H | H | Me | CO | O  | A1 | (E)-2-cyclopropylvinyl | H |   | Z | 3.90[a] |
| 35 | H | H | H | H | H | Me | CO | O  | A1 | [(benzyloxy)acetyl]amino | H |   | Z | 3.45[a] |
| 36 | H | H | H | H | H | Me | CO | O  | A1 | (2-methylpentanoyl)amino | H |   | Z | 3.45[a] |
| 37 | H | H | H | H | H | Me | CO | O  | A1 | hept-1-yn-1-yl | H |   | Z | 4.72[a] |
| 38 | H | H | H | H | H | Me | CO | O  | A1 | [(1-phenylethoxy)acetyl]amino | H |   | Z | 4.32[a] |
| 39 | H | H | H | H | H | Me | CO | O  | A1 | 3-phenylprop-1-yn-1-yl | H |   | Z | 4.07[a] |
| 40 | H | H | H | H | H | Me | CO | O  | A1 | (2-phenoxypropanoyl)amino | H |   | Z | 3.55[a] |
| 41 | H | H | H | H | H | Me | CO | O  | A1 | (1E)-3-phenylprop-1-en-1-yl | H |   | Z | 4.39[a] |
| 42 | H | H | H | H | H | Me | CO | O  | A1 | [(allyloxy)carbonyl]amino | H |   | Z | 3.02[a] |
| 43 | H | H | H | H | H | Me | O  | CO | A1 | tert-butylcarbamoyl | H |   | Z | 2.61[a] |

Measurement of logP values was performed according EEC directive 79/831 Annex V.A8 by HPLC (High Performance Liquid Chromatography) on reversed phase columns with the following methods:

[a] Measurement of LC-MS was done at pH 2.7 with 0.1% formic acid in water and with acetonitrile (contains 0.1% formic acid) as eluent with a linear gradient from 10% acetonitrile to 95% acetonitrile.

Calibration was done with not branched alkan2-ones (with 3 to 16 carbon atoms) with known logP-values (measurement of logP values using retention times with linear interpolation between successive alkanones). lambda-maX-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

Example 1: $^1$H-NMR (400.0 MHz, d$_6$-DMSO):

δ = 10.657 (0.6); 7.747 (2.9); 7.747 (0.9); 7.742 (3.5); 7.738 (2.7); 7.589 (0.6); 7.577 (0.5); 7.570 (1.8); 7.565 (0.7); 7.552 (1.5); 7.520 (2.6); 7.501 (3.3); 7.487 (0.6); 7.483 (1.3); 7.310 (2.6); 5.579 (7.7); 4.182 (2.0); 4.165 (4.3); 4.149 (2.1); 4.122 (0.4); 3.902 (5.6); 3.325 (51.4); 3.309 (1.0); 3.201 (0.4); 3.059 (16.0); 2.902 (1.6); 2.896 (3.6); 2.889 (1.7); 2.676 (0.4); 2.671 (0.5); 2.667 (0.4); 2.568 (1.3); 2.562 (1.4); 2.552 (2.7); 2.545 (2.7); 2.535 (1.5); 2.528 (1.6); 2.525 (1.7); 2.511 (34.7); 2.507 (70.2); 2.502 (93.2); 2.498 (69.1); 2.493 (34.9); 2.333 (0.4); 2.329 (0.6); 2.324 (0.4); 0.000 (2.7)

Example 2: $^1$H-NMR (400.1 MHz, d$_6$-DMSO):

δ = 8.364 (1.3); 8.358 (1.2); 7.956 (2.5); 7.711 (1.1); 7.693 (1.4); 7.689 (1.0); 7.595 (0.7); 7.577 (0.5); 7.537 (1.0); 7.518 (1.3); 7.500 (0.5); 7.155 (1.2); 7.148 (1.2); 6.338 (3.1); 3.564 (6.1); 3.351 (249.1); 3.328 (1.9); 2.894 (16.0); 2.734 (14.1); 2.511 (35.2); 2.506 (46.4); 2.502 (34.0)

Example 3: $^1$H-NMR (400.0 MHz, d$_6$-DMSO):

δ = 7.925 (6.4); 7.769 (2.6); 7.756 (0.7); 7.751 (3.2); 7.747 (2.3); 7.597 (0.5); 7.585 (0.4); 7.579 (1.7); 7.574 (0.6); 7.564 (0.9); 7.561 (1.3); 7.526 (2.4); 7.510 (1.7); 7.507 (3.1); 7.493 (0.5); 7.489 (1.2); 5.668 (8.8); 5.606 (0.3); 3.325 (85.9); 3.304 (0.8); 3.075 (16.0); 2.671 (0.4); 2.667 (0.3); 2.525 (1.0); 2.511 (25.8); 2.507 (53.4); 2.502 (71.5); 2.498 (52.3); 2.493 (25.7); 2.333 (0.3); 2.329 (0.5); 2.324 (0.3)

Example 4: $^1$H-NMR (400.1 MHz, d$_6$-DMSO):

δ = 7.869 (5.2); 7.685 (2.8); 7.667 (3.6); 7.663 (2.7); 7.591 (0.6); 7.580 (0.5); 7.573 (1.8); 7.567 (0.6); 7.558 (1.2); 7.555 (1.6); 7.525 (2.8); 7.506 (3.3); 7.489 (1.3); 5.605 (8.5); 3.714 (0.3); 3.706 (0.3); 3.687 (16.0); 3.308 (8.8); 2.523 (1.0); 2.505 (19.5); 2.501 (25.4); 2.496 (18.6); 2.474 (0.7); 1.571 (0.6); 1.563 (0.7); 1.559 (0.5); 1.550 (1.3); 1.542 (0.5); 1.538 (0.9); 1.530 (0.7); 1.517 (0.4); 1.246 (0.4); 0.922 (0.7); 0.911 (2.0); 0.905 (2.5); 0.895 (1.3); 0.891 (2.1); 0.884 (2.2); 0.875 (1.1); 0.858 (0.7); 0.761 (1.0); 0.751 (2.6); 0.745 (2.4); 0.739 (2.5); 0.733 (2.3); 0.722 (0.7); 0.000 (4.3)

Example 5: $^1$H-NMR (400.0 MHz, d$_6$-DMSO):

δ = 8.272 (2.4); 7.775 (1.1); 7.757 (1.3); 7.753 (1.0); 7.580 (0.7); 7.562 (0.6); 7.527 (1.0); 7.508 (1.3); 7.490 (0.5); 7.457 (0.8); 5.689 (3.3); 3.325 (29.8); 3.088 (6.4); 2.891 (0.8); 2.731 (0.8); 2.524 (0.5); 2.510 (10.9); 2.506 (22.2); 2.502 (29.7); 2.497 (22.0); 2.493 (11.1); 1.380 (16.0)

Example 6: $^1$H-NMR (400.0 MHz, d$_6$-DMSO):

δ = 10.236 (0.4); 7.758 (1.3); 7.740 (1.5); 7.570 (0.7); 7.552 (0.6); 7.520 (1.1); 7.501 (1.4); 7.483 (0.5); 7.256 (0.6); 5.565 (3.1); 3.902 (1.7); 3.328 (52.1); 3.058 (6.1); 2.506 (34.0); 2.502 (42.2); 2.498 (32.8); 1.460 (16.0); 0.000 (0.8)

Example 7: $^1$H-NMR (400.1 MHz, d$_6$-DMSO):

δ = 10.019 (0.8); 7.917 (0.9); 7.907 (3.2); 7.901 (3.0); 7.840 (0.3); 7.834 (0.3); 7.765 (0.4); 7.687 (3.2); 7.669 (4.0); 7.665 (3.0); 7.596 (0.8); 7.578 (2.2); 7.560 (1.8); 7.528 (3.1); 7.508 (3.7); 7.490 (1.5); 7.471 (0.7); 7.456 (0.5); 7.431 (1.1); 7.420 (0.5); 6.401 (1.4); 6.076 (7.3); 5.909 (0.5); 5.867 (0.7); 5.839 (0.7); 5.832 (0.9); 5.763 (2.7); 5.504 (0.7); 4.269 (0.5); 4.253 (1.0); 4.236 (0.5); 4.048 (2.6); 4.031 (5.1); 4.014 (2.6); 3.501 (0.3); 3.470 (16.0); 3.334 (166.8); 3.226 (0.5); 2.862 (0.7); 2.817 (0.4); 2.675 (0.5); 2.511 (58.3); 2.507 (76.4); 2.502 (57.5); 2.355 (0.5); 2.334 (0.7); 1.693 (0.3); 1.675 (0.5); 1.659 (0.4); 1.597 (1.6); 1.580 (2.3); 1.563 (1.7); 1.337 (1.8); 1.315 (4.6); 1.307 (5.2); 1.297 (6.0); 1.253 (0.7); 1.240 (0.9); 1.197 (0.3); 1.179 (0.4); 0.887 (3.7); 0.870 (7.2); 0.853 (2.8); 0.815 (0.7); 0.796 (0.4)

Example 9: $^1$H-NMR (400.0 MHz, d$_6$-DMSO):

δ = 8.301 (6.4); 8.074 (0.9); 8.053 (1.0); 7.773 (2.6); 7.760 (0.7); 7.755 (3.3); 7.751 (2.4); 7.597 (0.5); 7.594 (0.4); 7.585 (0.4); 7.579 (1.7); 7.573 (0.6); 7.563 (0.8); 7.560 (1.4); 7.557 (0.8); 7.525 (2.4); 7.509 (1.7); 7.506 (3.2); 7.492 (0.5); 7.488 (1.2); 7.485 (0.8); 5.692 (7.7); 3.754 (0.5); 3.744 (0.4); 3.732 (0.5); 3.325 (74.2); 3.299 (0.6); 3.089 (0.4); 3.078 (16.0); 2.891 (1.9); 2.731 (1.6); 2.676 (0.4); 2.671 (0.5); 2.667 (0.4); 2.524 (1.1); 2.520 (1.8); 2.511 (28.9); 2.507 (59.9); 2.502 (80.1); 2.497 (58.4); 2.493 (28.4); 2.333 (0.4); 2.329 (0.5); 2.324 (0.4); 1.778 (0.9); 1.764 (0.8); 1.747 (1.2); 1.720 (1.1); 1.689 (1.0); 1.604 (0.5); 1.573 (0.6); 1.390 (1.0); 1.384 (0.8); 1.357 (1.2); 1.334 (1.4); 1.309 (1.1); 1.279 (0.9); 1.247 (0.4); 1.131 (0.5); 1.108 (0.3); 1.101 (0.4)

Example 10: $^1$H-NMR (400.0 MHz, d$_6$-DMSO):

δ = 7.870 (5.9); 7.763 (3.2); 7.744 (3.6); 7.593 (0.6); 7.575 (1.8); 7.557 (1.5); 7.523 (2.7); 7.503 (3.4); 7.485 (1.4); 5.616 (8.5); 5.350 (0.3); 3.902 (3.0); 3.371 (0.7); 3.326 (75.6); 3.292 (0.7); 3.287 (0.8); 3.209 (0.9); 3.058 (16.0); 2.671 (0.6); 2.506 (82.4); 2.502 (103.5); 2.498 (81.3); 2.329 (0.7); 1.585 (0.4); 1.573 (0.7); 1.564 (0.8); 1.552 (1.4); 1.540 (0.9); 1.532 (0.9); 1.519 (0.5); 1.335 (0.6); 1.298 (0.5); 1.259 (1.3); 1.244 (0.7); 1.237 (0.9); 1.177 (0.4); 0.923 (0.8); 0.912 (2.2); 0.906 (2.9); 0.892 (2.4); 0.885 (2.6); 0.876 (1.2); 0.761 (1.0); 0.752 (2.7); 0.746 (2.8); 0.740 (3.0); 0.734 (2.8); 0.723 (0.9); 0.000 (2.1)

Example 11: $^1$H-NMR (400.0 MHz, d$_6$-DMSO):

δ = 10.493 (0.9); 7.765 (1.0); 7.747 (1.2); 7.743 (0.9); 7.632 (2.2); 7.574 (0.6); 7.556 (0.5); 7.524 (0.9); 7.505 (1.2); 7.487 (0.5); 5.607 (2.8); 3.902 (0.9); 3.328 (34.2); 3.052 (5.5); 2.507 (22.8); 2.502 (30.2); 2.498 (23.1); 1.210 (16.0); 1.159 (0.3); 0.000 (0.7)

-continued

Example 12: $^1$H-NMR (400.0 MHz, d$_6$-DMSO):

δ = 7.924 (0.4); 7.863 (5.1); 7.814 (0.4); 7.766 (2.6); 7.748 (3.3); 7.744 (2.4); 7.595 (0.5); 7.592 (0.3); 7.583 (0.4); 7.577 (1.7); 7.571 (0.6); 7.562 (0.9); 7.558 (1.4); 7.555 (0.7); 7.524 (2.4); 7.508 (1.8); 7.505 (3.3); 7.491 (0.6); 7.487 (1.4); 7.303 (8.8); 7.292 (10.9); 7.227 (0.7); 7.217 (1.1); 7.205 (1.2); 7.193 (0.7); 5.667 (0.6); 5.624 (7.9); 3.326 (98.3); 3.304 (0.5); 3.287 (0.6); 3.074 (1.2); 3.056 (16.0); 2.874 (1.2); 2.856 (3.3); 2.838 (2.2); 2.742 (2.1); 2.724 (3.2); 2.706 (1.2); 2.676 (0.4); 2.671 (0.5); 2.666 (0.4); 2.524 (1.1); 2.511 (29.4); 2.506 (60.6); 2.502 (80.6); 2.497 (58.0); 2.493 (27.8); 2.333 (0.4); 2.329 (0.6); 2.324 (0.4); 1.230 (0.4); 0.000 (0.3)

Example 13: $^1$H-NMR (400.0 MHz, d$_6$-DMSO):

δ = 8.150 (6.4); 7.781 (3.0); 7.763 (3.4); 7.759 (2.7); 7.664 (1.8); 7.659 (0.9); 7.651 (2.1); 7.642 (2.4); 7.634 (1.0); 7.629 (2.2); 7.600 (0.5); 7.588 (0.5); 7.581 (1.7); 7.576 (0.8); 7.563 (1.4); 7.531 (2.5); 7.511 (3.3); 7.494 (1.3); 7.321 (2.2); 7.316 (0.9); 7.299 (4.0); 7.282 (0.8); 7.277 (2.0); 5.684 (7.9); 3.903 (2.5); 3.328 (103.6); 3.085 (16.0); 3.028 (0.4); 2.676 (0.4); 2.672 (0.5); 2.667 (0.4); 2.507 (68.3); 2.503 (88.9); 2.498 (67.2); 2.334 (0.4); 2.329 (0.5); 2.325 (0.4); 0.000 (1.8)

Example 14: $^1$H-NMR (300.2 MHz, d$_6$-DMSO):

δ = 7.935 (4.6); 7.691 (4.5); 7.670 (5.8); 7.535 (4.4); 7.510 (4.8); 5.659 (10.3); 4.041 (1.0); 4.016 (1.0); 3.707 (16.0); 3.334 (14.0); 2.501 (12.9); 1.990 (3.9); 1.238 (0.5); 1.198 (1.1); 1.174 (2.1); 1.151 (1.1); 0.000 (3.3)

Example 15: $^1$H-NMR (400.0 MHz, d$_6$-DMSO):

δ = 8.497 (0.5); 8.482 (1.1); 8.467 (0.5); 8.315 (0.4); 8.303 (6.5); 7.773 (2.6); 7.761 (0.7); 7.755 (3.3); 7.752 (2.4); 7.599 (0.5); 7.596 (0.4); 7.586 (0.4); 7.580 (1.7); 7.575 (0.5); 7.565 (0.9); 7.562 (1.4); 7.559 (0.8); 7.527 (2.4); 7.512 (1.7); 7.508 (3.2); 7.494 (0.5); 7.490 (1.3); 7.487 (0.8); 7.301 (1.2); 7.283 (3.0); 7.270 (1.0); 7.265 (3.0); 7.236 (2.6); 7.232 (3.7); 7.215 (1.9); 7.206 (1.1); 7.188 (1.4); 7.174 (0.3); 7.170 (0.5); 5.681 (7.5); 3.519 (0.8); 3.503 (1.6); 3.482 (1.6); 3.467 (0.9); 3.325 (98.7); 3.279 (0.4); 3.094 (0.3); 3.054 (16.0); 2.891 (2.0); 2.857 (1.5); 2.838 (2.2); 2.820 (1.4); 2.731 (1.6); 2.675 (0.4); 2.671 (0.6); 2.666 (0.4); 2.524 (1.4); 2.520 (2.1); 2.511 (32.5); 2.506 (67.7); 2.502 (90.9); 2.497 (66.3); 2.493 (32.2); 2.333 (0.4); 2.329 (0.6); 2.324 (0.4); 0.000 (0.4)

Example 16: $^1$H-NMR (400.0 MHz, d$_6$-DMSO):

δ = 10.290 (2.8); 8.520 (5.8); 7.960 (0.5); 7.845 (3.5); 7.825 (3.8); 7.800 (3.4); 7.782 (3.8); 7.610 (0.6); 7.592 (1.9); 7.574 (1.6); 7.541 (2.9); 7.521 (3.8); 7.504 (1.4); 7.375 (2.1); 7.356 (3.8); 7.336 (2.4); 7.137 (1.2); 7.118 (2.0); 7.100 (0.9); 5.770 (8.8); 3.334 (109.7); 3.106 (16.0); 2.899 (2.8); 2.740 (2.6); 2.679 (0.6); 2.510 (99.3); 2.337 (0.6)

Example 17: $^1$H-NMR (400.0 MHz, d$_6$-DMSO):

δ = 11.331 (2.5); 7.827 (3.8); 7.775 (3.2); 7.757 (3.6); 7.754 (2.9); 7.595 (0.6); 7.576 (1.8); 7.558 (1.6); 7.527 (2.8); 7.508 (3.5); 7.490 (1.4); 7.463 (1.6); 7.444 (1.8); 7.394 (0.7); 7.376 (1.6); 7.360 (1.3); 7.294 (2.2); 7.283 (1.5); 7.275 (1.6); 7.265 (1.8); 7.246 (0.7); 5.628 (8.0); 3.902 (3.1); 3.330 (148.6); 3.080 (16.0); 2.672 (0.6); 2.506 (79.5); 2.502 (100.6); 2.498 (77.1); 2.377 (12.7); 2.333 (0.5); 2.329 (0.6); 0.000 (1.6)

Example 18: $^1$H-NMR (400.0 MHz, d$_6$-DMSO):

δ = 8.420 (0.5); 8.405 (1.0); 8.390 (0.5); 8.315 (0.4); 8.290 (6.4); 7.772 (2.7); 7.759 (0.8); 7.754 (3.3); 7.750 (2.4); 7.596 (0.5); 7.583 (0.4); 7.577 (1.7); 7.572 (0.6); 7.562 (0.9); 7.559 (1.4); 7.523 (2.4); 7.508 (1.7); 7.504 (3.2); 7.490 (0.5); 7.486 (1.2); 5.686 (7.7); 3.961 (0.4); 3.325 (87.9); 3.291 (0.4); 3.260 (0.8); 3.243 (2.0); 3.226 (2.0); 3.209 (0.9); 3.067 (16.0); 2.675 (0.4); 2.671 (0.6); 2.667 (0.4); 2.524 (1.1); 2.511 (32.5); 2.506 (67.4); 2.502 (90.1); 2.497 (65.8); 2.493 (32.3); 2.333 (0.4); 2.329 (0.6); 2.324 (0.4); 2.032 (0.3); 1.512 (0.8); 1.496 (1.3); 1.479 (1.0); 1.260 (7.4); 0.870 (1.6); 0.854 (5.4); 0.837 (1.8); 0.000 (0.4)

Example 19: $^1$H-NMR (400.0 MHz, d$_6$-DMSO):

δ = 11.257 (2.9); 7.762 (3.4); 7.743 (3.8); 7.590 (6.1); 7.571 (1.9); 7.553 (1.7); 7.520 (2.8); 7.501 (3.6); 7.483 (1.5); 7.320 (9.5); 7.313 (5.5); 7.307 (5.4); 7.287 (1.0); 7.278 (0.4); 7.254 (0.9); 7.247 (1.2); 7.240 (1.1); 7.232 (1.2); 7.224 (0.8); 7.218 (0.6); 7.210 (0.4); 5.605 (8.1); 3.902 (3.6); 3.661 (8.2); 3.326 (64.3); 3.168 (0.4); 3.116 (0.3); 3.049 (16.0); 2.671 (0.7); 2.506 (92.4); 2.502 (116.1); 2.498 (90.6); 2.329 (0.7); 0.000 (2.4)

Example 20: $^1$H-NMR (400.0 MHz, d$_6$-DMSO):

δ = 7.921 (5.1); 7.769 (2.5); 7.756 (0.7); 7.751 (3.2); 7.747 (2.3); 7.593 (0.5); 7.590 (0.4); 7.581 (0.4); 7.575 (1.6); 7.569 (0.5); 7.560 (0.8); 7.557 (1.3); 7.553 (0.7); 7.523 (2.3); 7.507 (1.6); 7.503 (3.0); 7.490 (0.5); 7.486 (1.2); 7.483 (0.7); 7.312 (1.0); 7.308 (0.5); 7.293 (2.7); 7.280 (0.8); 7.275 (2.6); 7.239 (2.3); 7.235 (3.2); 7.218 (1.8); 7.211 (0.9); 7.207 (0.9); 7.189 (1.4); 7.171 (0.5); 5.638 (7.7); 3.325 (62.7); 3.302 (0.6); 3.069 (16.0); 2.736 (1.5); 2.717 (2.2); 2.698 (1.6); 2.671 (0.4); 2.525 (1.0); 2.520 (1.4); 2.511 (22.8); 2.507 (47.4); 2.502 (63.5); 2.497 (46.0); 2.493 (22.1); 2.443 (1.6); 2.425 (3.6); 2.407 (1.8); 2.329 (0.4); 1.878 (0.5); 1.860 (1.4); 1.840 (1.7); 1.822 (1.4); 1.804 (0.4)

Example 21: $^1$H-NMR (400.0 MHz, d$_6$-DMSO):

δ = 7.885 (5.5); 7.766 (2.9); 7.748 (3.4); 7.745 (2.6); 7.594 (0.5); 7.576 (1.7); 7.558 (1.4); 7.524 (2.5); 7.504 (3.3); 7.487 (1.2); 5.629 (8.4); 3.902 (1.9); 3.372 (0.4); 3.330 (130.5); 3.065 (16.0); 2.672 (0.5); 2.667 (0.4); 2.507 (59.4); 2.502 (77.7); 2.498 (59.2); 2.446 (2.2); 2.429 (4.5); 2.411 (2.4); 2.333 (0.3); 2.329 (0.5); 2.325 (0.4); 1.555 (0.4); 1.539 (1.2); 1.532 (0.6); 1.520 (1.9); 1.515 (1.2); 1.502 (1.9); 1.484 (0.7); 1.465 (0.4); 1.447 (1.3); 1.429 (1.8); 1.409 (1.7); 1.392 (0.9); 0.923 (4.2); 0.905 (8.1); 0.887 (3.6); 0.000 (1.5)

Example 22: $^1$H-NMR (400.0 MHz, d$_6$-DMSO):

δ = 7.892 (5.4); 7.767 (2.7); 7.749 (3.2); 7.745 (2.4); 7.594 (0.5); 7.582 (0.4); 7.576 (1.6); 7.571 (0.6); 7.558 (1.3); 7.524 (2.3); 7.504 (3.0); 7.487 (1.1); 5.630 (7.9); 3.902 (2.0); 3.328 (85.7); 3.298 (0.4); 3.066 (16.0); 2.672 (0.4); 2.511 (23.5); 2.507 (46.4); 2.502 (60.9); 2.498 (45.2); 2.494 (23.0); 2.422 (2.2); 2.405 (4.6); 2.387 (2.4); 2.329 (0.3); 1.583 (1.3); 1.565 (2.7); 1.547 (2.8); 1.529 (1.4); 1.007 (4.3); 0.989 (8.5); 0.970 (3.8); 0.000 (1.6)

Example 23: $^1$H-NMR (400.0 MHz, d$_6$-DMSO):

δ = 8.507 (0.8); 8.316 (0.5); 8.139 (0.8); 8.121 (0.8); 8.117 (0.7); 7.943 (3.9); 7.883 (2.4); 7.797 (0.5); 7.768 (2.9); 7.750 (3.5); 7.730 (0.8); 7.726 (0.6); 7.648 (0.7); 7.638 (0.4); 7.628 (0.9); 7.620 (0.5); 7.609 (0.5); 7.595 (0.6); 7.577 (1.9); 7.559 (1.6); 7.525 (2.8); 7.506 (3.8); 7.488 (1.7); 7.083 (0.3); 5.692 (1.1); 5.638 (4.7); 5.627 (3.4); 5.548 (2.8); 3.902 (8.3); 3.371 (5.6); 3.325 (104.0);

3.300 (1.3); 3.209 (2.5); 3.200 (0.7); 3.103 (0.3); 3.086 (2.2); 3.079 (0.9); 3.067 (11.2); 3.065 (9.8); 2.826 (0.4); 2.809 (0.6); 2.792 (0.5); 2.676 (0.7); 2.671 (0.9); 2.667 (0.7); 2.524 (2.1); 2.511 (60.2); 2.507 (121.9); 2.502 (161.9); 2.498 (121.7); 2.493 (63.1); 2.446 (0.8); 2.333 (0.8); 2.329 (1.0); 2.324 (0.8); 2.086 (0.4); 1.483 (0.4); 1.474 (0.4); 1.463 (1.8); 1.454 (16.0); 1.397 (0.3); 1.245 (0.3); 1.235 (0.4); 1.215 (7.3); 1.198 (7.2); 1.066 (0.3); 0.000 (4.2)

Example 24: $^1$H-NMR (400.0 MHz, $d_6$-DMSO):

δ = 7.769 (2.7); 7.751 (3.3); 7.748 (2.5); 7.589 (0.5); 7.586 (0.4); 7.577 (5.0); 7.571 (1.9); 7.553 (1.4); 7.519 (2.4); 7.500 (3.2); 7.482 (1.2); 7.479 (1.0); 6.410 (1.3); 6.381 (1.4); 5.735 (0.6); 5.717 (1.2); 5.706 (0.6); 5.698 (0.6); 5.688 (1.2); 5.669 (0.6); 5.652 (8.1); 5.637 (0.5); 3.902 (2.3); 3.333 (200.1); 3.077 (0.8); 3.054 (16.0); 3.043 (0.7); 2.676 (0.4); 2.672 (0.5); 2.667 (0.4); 2.593 (0.6); 2.589 (0.6); 2.574 (1.6); 2.571 (1.7); 2.557 (1.8); 2.553 (1.8); 2.538 (0.9); 2.534 (1.0); 2.525 (1.3); 2.511 (30.5); 2.507 (61.0); 2.503 (80.2); 2.498 (59.5); 2.494 (30.2); 2.334 (0.3); 2.329 (0.5); 2.325 (0.4); 1.412 (1.0); 1.406 (0.7); 1.394 (1.6); 1.375 (1.4); 1.357 (0.7); 1.345 (0.4); 1.327 (1.1); 1.309 (1.6); 1.290 (1.4); 1.272 (0.8); 1.256 (0.4); 0.892 (0.4); 0.871 (4.0); 0.853 (7.3); 0.835 (3.0); 0.000 (1.7)

Example 25: $^1$H-NMR (400.0 MHz, $d_6$-DMSO):

δ = 8.315 (0.5); 7.880 (11.0); 7.681 (5.3); 7.664 (6.5); 7.660 (5.0); 7.571 (1.0); 7.567 (0.7); 7.559 (0.7); 7.552 (3.2); 7.547 (1.0); 7.537 (1.8); 7.534 (2.8); 7.507 (5.1); 7.488 (6.1); 7.474 (1.0); 7.470 (2.2); 7.467 (1.4); 5.568 (15.5); 3.902 (4.2); 3.333 (270.5); 2.676 (0.7); 2.672 (1.0); 2.667 (0.7); 2.542 (1.5); 2.511 (62.6); 2.507 (124.8); 2.502 (164.5); 2.498 (122.0); 2.494 (61.7); 2.447 (4.0); 2.430 (8.5); 2.413 (4.5); 2.334 (0.7); 2.329 (1.0); 2.325 (0.7); 1.557 (0.6); 1.542 (2.2); 1.535 (1.1); 1.523 (3.5); 1.517 (2.1); 1.505 (3.5); 1.487 (1.4); 1.468 (0.8); 1.450 (2.4); 1.438 (1.5); 1.432 (3.4); 1.420 (1.6); 1.412 (3.1); 1.394 (1.7); 1.377 (0.4); 1.336 (0.5); 1.235 (0.6); 1.225 (0.7); 0.925 (8.3); 0.907 (16.0); 0.889 (6.8); 0.000 (3.0)

Example 26: $^1$H-NMR (400.0 MHz, $d_6$-DMSO):

δ = 13.035 (0.5); 13.027 (0.5); 7.888 (10.0); 7.683 (5.9); 7.665 (6.9); 7.572 (1.0); 7.553 (3.3); 7.535 (2.9); 7.508 (5.4); 7.489 (6.5); 7.471 (2.3); 5.571 (16.0); 3.902 (3.2); 3.332 (193.6); 2.671 (1.0); 2.567 (0.6); 2.506 (123.2); 2.502 (152.9); 2.499 (119.8); 2.424 (4.6); 2.406 (9.3); 2.389 (4.9); 2.329 (0.9); 1.603 (0.6); 1.585 (2.8); 1.567 (5.6); 1.549 (5.7); 1.531 (3.0); 1.514 (0.7); 1.009 (8.2); 0.991 (15.6); 0.973 (7.2); 0.000 (2.2)

Example 27: $^1$H-NMR (400.0 MHz, $d_6$-DMSO):

δ = 11.008 (2.6); 7.769 (2.9); 7.751 (3.5); 7.747 (2.7); 7.694 (5.8); 7.594 (0.5); 7.581 (0.4); 7.575 (1.7); 7.557 (1.5); 7.525 (2.5); 7.506 (3.3); 7.488 (1.2); 7.116 (0.6); 7.098 (1.4); 7.077 (1.9); 7.057 (1.5); 6.890 (1.9); 6.870 (1.7); 6.863 (1.2); 6.844 (1.7); 6.826 (0.8); 5.641 (0.4); 5.620 (7.6); 4.816 (1.0); 4.808 (1.2); 4.795 (1.2); 4.787 (1.1); 3.902 (5.3); 3.330 (151.7); 3.174 (0.6); 3.163 (0.6); 3.060 (16.0); 3.040 (0.9); 2.813 (0.6); 2.797 (0.6); 2.790 (0.6); 2.775 (0.5); 2.742 (0.5); 2.729 (1.1); 2.715 (0.6); 2.688 (0.5); 2.672 (0.8); 2.507 (83.1); 2.502 (108.2); 2.498 (81.7); 2.333 (0.5); 2.329 (0.6); 2.325 (0.5); 2.215 (0.5); 2.207 (0.5); 2.194 (0.5); 2.180 (0.7); 2.172 (0.7); 2.077 (0.4); 2.070 (0.5); 2.056 (0.7); 2.048 (0.4); 2.034 (0.6); 2.022 (0.4); 1.235 (0.4); 0.000 (1.9)

Example 28: $^1$H-NMR (400.0 MHz, $d_6$-DMSO):

δ = 11.178 (2.2); 7.768 (2.9); 7.750 (3.3); 7.746 (2.6); 7.658 (4.9); 7.594 (0.5); 7.582 (0.4); 7.575 (1.7); 7.557 (1.4); 7.525 (2.5); 7.506 (3.2); 7.492 (0.6); 7.488 (1.2); 7.316 (1.8); 7.297 (2.9); 7.276 (2.3); 6.971 (1.4); 6.963 (3.2); 6.955 (2.6); 6.941 (3.1); 5.619 (7.6); 4.746 (8.3); 3.902 (5.7); 3.363 (0.4); 3.328 (147.9); 3.310 (1.4); 3.175 (0.4); 3.162 (0.4); 3.122 (0.4); 3.058 (16.0); 2.676 (0.5); 2.671 (0.6); 2.667 (0.5); 2.511 (39.2); 2.507 (79.0); 2.502 (105.0); 2.498 (79.1); 2.333 (0.4); 2.329 (0.6); 2.324 (0.5); 1.206 (0.3); 1.189 (0.4); 0.000 (2.6)

Example 29: $^1$H-NMR (400.0 MHz, $d_6$-DMSO):

δ = 9.935 (0.5); 8.778 (0.5); 8.315 (0.4); 7.776 (2.9); 7.758 (3.7); 7.754 (3.1); 7.744 (1.1); 7.731 (0.6); 7.590 (0.6); 7.587 (0.6); 7.571 (1.9); 7.550 (5.9); 7.520 (2.9); 7.504 (2.6); 7.500 (3.8); 7.483 (1.6); 7.338 (0.7); 6.296 (1.5); 6.267 (1.7); 5.733 (0.7); 5.651 (7.8); 5.635 (0.6); 5.625 (0.5); 5.613 (1.3); 5.560 (1.1); 5.536 (1.1); 5.531 (1.0); 5.507 (1.0); 3.902 (5.1); 3.372 (2.3); 3.331 (160.9); 3.162 (0.4); 3.133 (0.5); 3.107 (0.6); 3.093 (1.6); 3.087 (0.8); 3.080 (1.2); 3.077 (0.7); 3.060 (1.0); 3.049 (16.0); 3.038 (1.9); 2.676 (0.5); 2.672 (0.7); 2.667 (0.5); 2.511 (43.8); 2.507 (88.7); 2.503 (117.6); 2.498 (88.6); 2.494 (46.0); 2.334 (0.6); 2.329 (0.7); 2.325 (0.6); 1.727 (0.4); 1.679 (1.9); 1.673 (1.9); 1.649 (2.3); 1.582 (0.8); 1.555 (0.4); 1.538 (0.4); 1.515 (0.5); 1.498 (0.4); 1.317 (0.4); 1.285 (1.0); 1.254 (1.3); 1.232 (1.0); 1.224 (1.0); 1.206 (0.9); 1.177 (1.0); 1.146 (1.3); 1.141 (1.2); 1.116 (1.4); 1.112 (1.5); 1.085 (1.2); 1.058 (0.5); 1.048 (0.4); 0.000 (2.9)

Example 30: $^1$H-NMR (400.0 MHz, $d_6$-DMSO):

δ = 7.770 (2.8); 7.752 (3.3); 7.749 (2.7); 7.589 (0.6); 7.587 (0.5); 7.575 (5.0); 7.553 (1.5); 7.519 (2.5); 7.500 (3.3); 7.482 (1.3); 7.479 (1.1); 6.409 (1.2); 6.380 (1.4); 5.737 (0.6); 5.719 (1.2); 5.708 (0.6); 5.700 (0.6); 5.689 (1.1); 5.671 (0.6); 5.650 (8.0); 5.637 (0.6); 5.613 (0.5); 3.902 (2.4); 3.371 (0.5); 3.333 (198.5); 3.300 (0.7); 3.077 (1.1); 3.055 (16.0); 3.043 (1.3); 2.672 (0.6); 2.667 (0.4); 2.582 (0.6); 2.578 (0.7); 2.564 (1.7); 2.560 (1.8); 2.545 (1.8); 2.542 (1.9); 2.512 (28.8); 2.507 (58.4); 2.503 (77.5); 2.498 (57.9); 2.494 (29.5); 2.329 (0.4); 2.325 (0.3); 1.426 (0.9); 1.408 (1.3); 1.390 (1.0); 1.373 (0.4); 1.296 (0.7); 1.281 (3.0); 1.271 (2.9); 1.263 (4.0); 1.245 (1.3); 0.871 (0.5); 0.856 (2.0); 0.839 (5.1); 0.821 (1.6); 0.000 (1.5)

Example 31: $^1$H-NMR (400.0 MHz, $d_6$-DMSO):

δ = 7.882 (5.8); 7.767 (3.2); 7.749 (3.7); 7.745 (2.9); 7.594 (0.6); 7.576 (1.8); 7.558 (1.5); 7.524 (2.7); 7.505 (3.5); 7.487 (1.3); 5.630 (8.5); 3.902 (2.1); 3.330 (150.6); 3.068 (16.0); 2.668 (0.9); 2.656 (0.7); 2.646 (0.9); 2.636 (0.7); 2.623 (0.5); 2.507 (69.3); 2.502 (87.5); 2.498 (67.1); 2.329 (0.5); 1.830 (1.1); 1.821 (1.1); 1.806 (1.2); 1.677 (1.3); 1.663 (1.5); 1.655 (1.3); 1.505 (1.1); 1.494 (1.2); 1.474 (1.6); 1.451 (1.3); 1.429 (0.6); 1.421 (0.6); 1.378 (0.5); 1.354 (1.2); 1.330 (2.7); 1.310 (1.5); 0.000 (1.5)

Example 32: $^1$H-NMR (400.0 MHz, $d_6$-DMSO):

δ = 13.020 (0.4); 13.007 (0.3); 8.315 (0.4); 7.876 (12.8); 7.680 (6.3); 7.662 (7.3); 7.659 (6.4); 7.569 (1.1); 7.550 (3.7); 7.532 (3.3); 7.505 (6.1); 7.486 (7.3); 7.469 (2.6); 5.566 (16.0); 3.902 (6.0); 3.331 (166.2); 3.169 (1.3); 2.676 (1.2); 2.671 (1.8); 2.656 (1.3); 2.646 (1.9); 2.637 (1.3); 2.624 (1.1); 2.615 (0.6); 2.507 (137.9); 2.502 (180.7); 2.498 (138.8); 2.333 (0.8); 2.329 (1.1); 2.325 (0.9); 1.833 (2.1); 1.824 (2.3); 1.809 (2.5); 1.802 (2.4); 1.680 (2.6); 1.666 (3.1); 1.658 (2.7); 1.509 (2.3); 1.496 (2.4); 1.476 (3.2); 1.453 (2.6); 1.431 (1.1); 1.423 (1.2); 1.379 (0.9); 1.356 (2.4); 1.331 (5.6); 1.310 (3.1); 1.259 (0.4); 1.235 (0.6); 0.000 (3.3)

Example 33: $^1$H-NMR (400.0 MHz, $d_6$-DMSO):

δ = 13.034 (0.4); 8.526 (0.3); 8.315 (0.5); 7.881 (11.3); 7.682 (5.6); 7.664 (6.9); 7.661 (5.3); 7.571 (1.1); 7.553 (3.5); 7.534 (3.0); 7.507 (5.5); 7.488 (6.6); 7.470 (2.5); 5.633 (0.6); 5.569 (16.0); 3.902 (5.4); 3.332 (216.3); 3.169 (0.3); 2.676 (0.8); 2.672 (1.1); 2.667 (0.8); 2.542 (0.5); 2.507 (146.4); 2.502 (190.7); 2.498 (141.7); 2.440 (4.2); 2.422 (8.8); 2.405 (4.5); 2.334 (0.9); 2.329 (1.2); 2.325 (1.0); 1.576 (0.7); 1.559 (2.3); 1.541 (3.6); 1.522 (3.3); 1.504 (1.3); 1.421 (0.9); 1.406 (2.1); 1.398 (1.8); 1.389 (2.4); 1.383

-continued (2.6); 1.374 (1.8); 1.366 (2.6); 1.350 (2.2); 1.343 (2.7); 1.328 (3.3); 1.309 (2.8); 1.289 (1.6); 1.273 (0.7); 1.259 (0.5); 1.235 (0.9); 0.902 (7.8); 0.884 (14.6); 0.867 (6.1); 0.835 (0.4); 0.000 (4.1)

Example 34: $^1$H-NMR (400.0 MHz, $d_6$-DMSO):

δ = 7.766 (2.9); 7.748 (3.3); 7.745 (2.8); 7.585 (5.4); 7.571 (1.8); 7.553 (1.5); 7.520 (2.6); 7.500 (3.3); 7.483 (1.3); 6.286 (2.0); 6.257 (2.1); 5.666 (8.2); 5.615 (0.7); 5.053 (1.2); 5.025 (1.7); 4.998 (1.2); 3.902 (3.2); 3.388 (0.4); 3.333 (234.5); 3.059 (16.0); 3.049 (0.8); 2.765 (0.4); 2.754 (0.6); 2.741 (0.6); 2.728 (0.6); 2.717 (0.4); 2.676 (0.4); 2.672 (0.6); 2.667 (0.4); 2.507 (73.2); 2.503 (94.2); 2.498 (71.2); 2.333 (0.4); 2.329 (0.5); 2.325 (0.4); 0.797 (0.7); 0.787 (1.8); 0.781 (2.0); 0.767 (1.8); 0.761 (2.0); 0.752 (0.8); 0.444 (0.7); 0.434 (2.2); 0.429 (2.2); 0.423 (2.1); 0.418 (2.2); 0.407 (0.6); 0.000 (1.6)

Example 35: $^1$H-NMR (400.0 MHz, $d_6$-DMSO):

δ = 10.795 (2.2); 8.315 (0.3); 7.765 (2.8); 7.747 (3.3); 7.744 (2.5); 7.671 (4.8); 7.592 (0.5); 7.580 (0.4); 7.574 (1.7); 7.568 (0.6); 7.555 (1.4); 7.523 (2.5); 7.504 (3.2); 7.486 (1.3); 7.395 (0.7); 7.380 (8.2); 7.374 (4.1); 7.364 (3.9); 7.344 (0.9); 7.324 (0.7); 7.318 (1.0); 7.311 (0.8); 7.303 (1.0); 7.294 (0.4); 7.288 (0.4); 5.607 (7.6); 4.587 (9.0); 4.155 (8.9); 3.902 (7.5); 3.372 (0.6); 3.332 (247.6); 3.053 (16.0); 2.676 (0.4); 2.671 (0.6); 2.667 (0.5); 2.541 (0.4); 2.524 (2.0); 2.511 (40.1); 2.507 (79.9); 2.502 (105.0); 2.498 (78.2); 2.494 (39.9); 2.334 (0.5); 2.329 (0.6); 2.325 (0.4); 0.000 (1.9)

Example 36: $^1$H-NMR (400.0 MHz, $d_6$-DMSO):

δ = 10.951 (2.6); 7.766 (3.2); 7.748 (3.6); 7.631 (5.9); 7.592 (0.6); 7.574 (1.8); 7.556 (1.5); 7.524 (2.7); 7.505 (3.4); 7.487 (1.3); 5.599 (8.3); 3.902 (2.2); 3.333 (204.1); 3.055 (16.0); 2.672 (0.6); 2.605 (0.5); 2.586 (0.8); 2.570 (0.9); 2.553 (0.8); 2.507 (78.5); 2.503 (99.7); 2.499 (75.7); 2.329 (0.6); 1.588 (0.4); 1.578 (0.6); 1.565 (0.6); 1.557 (0.7); 1.543 (0.6); 1.327 (0.5); 1.315 (0.6); 1.302 (0.9); 1.288 (0.8); 1.283 (0.8); 1.269 (1.2); 1.258 (0.9); 1.248 (1.2); 1.231 (1.4); 1.214 (1.0); 1.201 (0.5); 1.197 (0.5); 1.188 (0.4); 1.061 (6.7); 1.044 (6.6); 0.870 (3.6); 0.852 (6.8); 0.834 (2.8); 0.000 (1.7)

Example 37: $^1$H-NMR (400.0 MHz, $d_6$-DMSO):

δ = 7.885 (5.5); 7.766 (2.9); 7.748 (3.4); 7.745 (2.5); 7.594 (0.5); 7.582 (0.5); 7.576 (1.7); 7.571 (0.6); 7.558 (1.4); 7.524 (2.6); 7.504 (3.3); 7.486 (1.3); 5.695 (0.4); 5.629 (8.2); 3.902 (1.9); 3.371 (1.1); 3.335 (221.9); 3.299 (0.8); 3.082 (0.8); 3.065 (16.0); 2.676 (0.4); 2.672 (0.5); 2.667 (0.4); 2.507 (64.0); 2.503 (84.4); 2.498 (63.5); 2.438 (2.1); 2.421 (4.4); 2.403 (2.2); 2.334 (0.4); 2.329 (0.5); 2.325 (0.4); 1.573 (0.4); 1.556 (1.1); 1.538 (1.8); 1.519 (1.6); 1.501 (0.6); 1.419 (0.4); 1.403 (1.0); 1.395 (0.9); 1.386 (1.1); 1.380 (1.3); 1.375 (1.0); 1.371 (0.9); 1.362 (1.3); 1.341 (1.3); 1.325 (1.6); 1.306 (1.4); 1.287 (0.7); 0.900 (3.8); 0.882 (7.2); 0.864 (2.9); 0.000 (0.9)

Example 38: $^1$H-NMR (400.0 MHz, $d_6$-DMSO):

δ = 10.623 (2.5); 7.763 (2.9); 7.745 (3.5); 7.741 (2.6); 7.650 (5.1); 7.592 (0.5); 7.580 (0.4); 7.573 (1.8); 7.568 (0.7); 7.555 (1.5); 7.523 (2.6); 7.503 (3.4); 7.486 (1.4); 7.368 (7.9); 7.357 (12.5); 7.309 (0.9); 7.298 (1.3); 7.287 (1.4); 7.279 (0.5); 7.275 (0.8); 5.600 (7.7); 4.617 (0.5); 4.601 (1.7); 4.585 (1.8); 4.569 (0.5); 3.987 (0.6); 3.949 (4.2); 3.940 (4.3); 3.902 (8.6); 3.400 (0.4); 3.387 (0.5); 3.371 (1.1); 3.337 (377.4); 3.051 (16.0); 2.676 (0.5); 2.672 (0.7); 2.667 (0.5); 2.542 (0.3); 2.511 (44.4); 2.507 (89.3); 2.503 (118.7); 2.498 (89.5); 2.334 (0.5); 2.329 (0.7); 2.325 (0.5); 1.426 (6.8); 1.410 (6.8); 1.129 (0.4); 1.115 (0.4); 0.000 (0.5)

Example 39: $^1$H-NMR (400.0 MHz, $d_6$-DMSO):

δ = 8.811 (0.4); 8.722 (1.1); 8.507 (2.9); 8.314 (0.7); 8.179 (0.5); 8.161 (0.6); 8.158 (0.5); 8.139 (0.5); 8.121 (0.5); 8.117 (0.5); 7.984 (3.3); 7.956 (0.4); 7.938 (0.4); 7.935 (0.5); 7.896 (0.3); 7.816 (0.4); 7.805 (0.4); 7.797 (0.7); 7.786 (1.1); 7.782 (0.9); 7.768 (3.3); 7.755 (2.4); 7.750 (3.2); 7.746 (2.3); 7.716 (1.4); 7.711 (0.7); 7.670 (0.6); 7.649 (0.9); 7.628 (0.9); 7.609 (0.5); 7.604 (0.4); 7.594 (0.8); 7.576 (1.9); 7.570 (1.2); 7.560 (1.7); 7.557 (1.8); 7.523 (2.9); 7.504 (3.9); 7.486 (2.2); 7.433 (0.4); 7.425 (0.4); 7.402 (1.0); 7.385 (2.5); 7.377 (2.5); 7.359 (2.2); 7.339 (0.9); 7.294 (0.4); 7.283 (0.8); 7.265 (1.0); 7.249 (0.5); 7.211 (0.6); 7.083 (0.5); 6.956 (0.4); 5.778 (0.5); 5.740 (1.4); 5.692 (3.4); 5.642 (5.0); 3.908 (4.3); 3.902 (16.0); 3.501 (0.4); 3.372 (5.4); 3.337 (499.1); 3.200 (0.6); 3.105 (3.4); 3.087 (7.5); 3.067 (10.2); 3.056 (0.9); 3.037 (0.4); 3.010 (0.3); 2.989 (0.4); 2.677 (1.0); 2.672 (1.3); 2.667 (1.0); 2.663 (0.5); 2.542 (0.8); 2.525 (3.6); 2.512 (81.9); 2.507 (165.4); 2.503 (218.2); 2.498 (162.5); 2.494 (83.0); 2.334 (0.9); 2.330 (1.3); 2.325 (0.9); 1.235 (0.5); 0.000 (3.7)

Example 40: $^1$H-NMR (400.0 MHz, $d_6$-DMSO):

δ = 11.287 (2.6); 7.765 (3.0); 7.747 (3.5); 7.743 (2.8); 7.630 (5.9); 7.593 (0.8); 7.575 (1.7); 7.556 (1.5); 7.523 (2.6); 7.504 (3.4); 7.486 (1.4); 7.291 (1.8); 7.270 (3.1); 7.251 (2.3); 6.942 (1.1); 6.923 (2.3); 6.914 (3.6); 6.894 (3.2); 5.611 (7.6); 5.008 (0.5); 4.992 (1.6); 4.975 (1.6); 4.959 (0.5); 3.902 (8.5); 3.335 (273.8); 3.055 (16.0); 2.676 (0.5); 2.672 (0.6); 2.667 (0.5); 2.507 (83.2); 2.503 (107.7); 2.498 (82.5); 2.334 (0.5); 2.329 (0.6); 2.325 (0.5); 1.525 (6.2); 1.508 (6.2); 1.236 (0.4); 0.000 (1.7)

Example 41: $^1$H-NMR (400.0 MHz, $d_6$-DMSO):

δ = 9.934 (0.4); 8.778 (0.3); 8.318 (0.5); 7.832 (0.4); 7.787 (0.4); 7.757 (3.5); 7.745 (1.4); 7.740 (3.7); 7.736 (3.2); 7.628 (0.3); 7.601 (0.4); 7.586 (1.0); 7.582 (1.5); 7.567 (2.3); 7.547 (1.5); 7.526 (0.9); 7.513 (3.3); 7.494 (4.2); 7.476 (1.9); 7.333 (1.3); 7.314 (3.4); 7.308 (2.0); 7.296 (3.0); 7.271 (0.4); 7.250 (4.0); 7.232 (3.1); 7.212 (1.8); 7.194 (0.8); 6.661 (0.6); 6.643 (0.9); 6.622 (0.7); 6.605 (1.5); 6.587 (0.8); 6.508 (2.0); 6.469 (1.1); 5.742 (0.8); 5.733 (0.6); 5.668 (0.4); 5.641 (0.4); 5.624 (8.1); 5.610 (1.1); 5.561 (0.3); 4.002 (0.4); 3.997 (0.4); 3.903 (7.4); 3.529 (2.7); 3.511 (2.7); 3.371 (2.8); 3.337 (636.4); 3.282 (1.4); 3.261 (0.6); 3.249 (0.5); 3.236 (0.5); 3.200 (0.4); 3.175 (0.6); 3.162 (0.3); 3.112 (1.7); 3.107 (0.9); 3.092 (1.2); 3.086 (0.8); 3.074 (1.0); 3.059 (16.0); 3.044 (1.0); 3.040 (0.9); 3.034 (2.2); 3.018 (0.7); 2.991 (0.3); 2.963 (0.6); 2.949 (0.5); 2.676 (0.9); 2.671 (1.2); 2.667 (1.0); 2.511 (77.0); 2.507 (153.7); 2.502 (203.9); 2.498 (154.9); 2.333 (0.9); 2.329 (1.2); 2.325 (0.9); 1.234 (1.1); 0.008 (0.5); 0.000 (13.3); −0.008 (0.5)

Example 42: $^1$H-NMR (400.0 MHz, $d_6$-DMSO):

δ = 10.654 (0.7); 7.769 (0.4); 7.761 (2.7); 7.748 (0.8); 7.743 (3.3); 7.739 (2.4); 7.589 (0.5); 7.586 (0.3); 7.578 (0.4); 7.571 (1.7); 7.565 (0.5); 7.556 (0.9); 7.553 (1.4); 7.550 (0.8); 7.521 (2.5); 7.505 (1.8); 7.501 (3.2); 7.488 (0.5); 7.484 (1.3); 7.481 (0.8); 7.307 (2.5); 7.251 (0.6); 7.232 (0.4); 7.142 (0.7); 7.122 (0.5); 5.994 (0.7); 5.981 (0.6); 5.967 (0.8); 5.964 (0.5); 5.954 (0.4); 5.951 (0.9); 5.937 (0.7); 5.924 (0.9); 5.911 (0.4); 5.583 (7.6); 5.376 (0.5); 5.372 (1.5); 5.368 (1.5); 5.364 (0.6); 5.333 (0.4); 5.329 (1.2); 5.325 (1.3); 5.320 (0.5); 5.238 (1.3); 5.235 (1.3); 5.212 (1.2); 5.208 (1.3); 4.624 (1.7); 4.621 (2.9); 4.617 (1.9); 4.611 (1.8); 4.607 (2.9); 4.604 (1.8); 3.357 (7.7); 3.308 (1.0); 3.093 (0.4); 3.056 (16.0); 2.891 (1.2); 2.731 (1.0); 2.676 (0.4); 2.671 (0.5); 2.666 (0.4); 2.524 (0.9); 2.519 (1.4); 2.511 (28.0); 2.506 (59.4); 2.502 (80.5); 2.497 (59.2); 2.493 (29.2); 2.333 (0.4); 2.329 (0.5); 2.324 (0.4)

Example 43: $^1$H-NMR (400.0 MHz, $d_6$-DMSO):

δ = 8.274 (2.4); 7.697 (1.1); 7.679 (1.4); 7.676 (1.1); 7.580 (0.7); 7.562 (0.6); 7.532 (1.0); 7.512 (1.3); 7.495 (0.5); 7.469 (0.8); 5.678 (3.1); 3.903 (3.6); 3.714 (6.3); 3.345 (150.2); 2.507 (31.1); 2.503 (40.9); 2.499 (31.2); 1.380 (16.0); 0.000 (1.2)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

(IV)

In table 2, we use this following abbreviation for specified claimed elements "$A^1$, $A^{14}$" of the generic structure (IV) of the invention:

TABLE 2

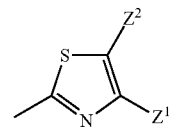
$A^1$

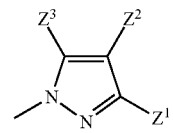
$A^{14}$

| Example | Y1 | Y2 | Y3 | Y4 | Y5 | A | Z1 | Z2 | Z3 | logP |
|---|---|---|---|---|---|---|---|---|---|---|
| IV-1 | H | H | H | H | H | A14 | NO2 | H | H | 2.90[a] |
| IV-2 | H | H | H | H | H | A1 | CO2Me | H | | 2.80[a] |
| IV-3 | H | H | H | H | H | A1 | Br | H | | 3.61[a] |
| IV-4 | H | H | H | H | H | A14 | NH2 | H | H | 1.86[a] |
| IV-5 | H | H | H | H | H | A1 | 5-phenylpent-1-yn-1-yl | H | | 5.19[a] |
| IV-6 | H | H | H | H | H | A1 | pent-1-yn-1-yl | H | | 4.41[a] |
| IV-7 | H | H | H | H | H | A1 | hex-1-yn-1-yl | H | | 4.83[a] |
| IV-8 | H | H | H | H | H | A1 | cyclopropylethynyl | H | | 4.04[a] |
| IV-9 | H | H | H | H | H | A1 | cyclohexylethynyl | H | | 5.42[a] |
| IV-10 | H | H | H | H | H | A1 | hept-1-yn-1-yl | H | | 5.27[a] |

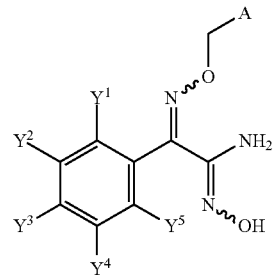
(V)

In table 3, we use this following abbreviation for specified claimed elements "$A^1$, $A^{14}$" of the generic structure (V) of the invention:

TABLE 3

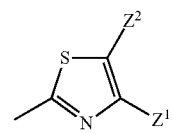
$A^1$

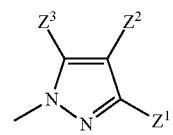
$A^{14}$

| Example | Y1 | Y2 | Y3 | Y4 | Y5 | A | Z1 | Z2 | Z3 | logP |
|---|---|---|---|---|---|---|---|---|---|---|
| V-1 | H | H | H | H | H | A14 | NH2 | H | H | 0.65[a] |
| V-2 | H | H | H | H | H | A1 | Br | H | | 1.86[a] |

TABLE 3-continued

A¹

A¹⁴

| Example | Y1 | Y2 | Y3 | Y4 | Y5 | A | Z1 | Z2 | Z3 | logP |
|---|---|---|---|---|---|---|---|---|---|---|
| V-3 | H | H | H | H | H | A1 | pent-1-yn-1-yl | H | | 2.59[a] |
| V-4 | H | H | H | H | H | A1 | hex-1-yn-1-yl | H | | 2.98[a] |
| V-5 | H | H | H | H | H | A1 | cyclohexylethynyl | H | | 3.42[a] |
| V-6 | H | H | H | H | H | A1 | hept-1-yn-1-yl | H | | 3.37[a] |

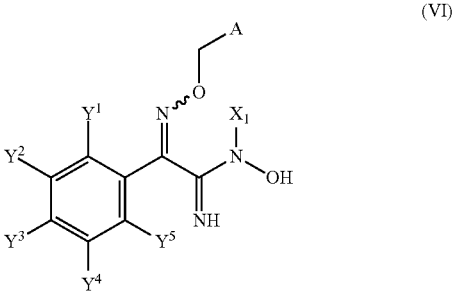

(VI)

In table 4, we use this following abbreviation for specified claimed elements "$A^1$, $A^{14}$" of the generic structure (VI) of the invention:

TABLE 4

A¹

A¹⁴

| Example | Y1 | Y2 | Y3 | Y4 | Y5 | X1 | A | Z1 | Z2 | Z3 | logP |
|---|---|---|---|---|---|---|---|---|---|---|---|
| VI-1 | H | H | H | H | H | Me | A14 | NO2 | H | H | 1.15[a] |
| VI-2 | H | H | H | H | H | Me | A1 | Br | H | | 1.49[a] |

Measurement of logP values was performed according EEC directive 79/831 Annex V.A8 by HPLC (High Performance Liquid Chromatography) on reversed phase columns with the following methods:

[a] Measurement of LC-MS was done at pH 2.7 with 0.1% formic acid in water and with acetonitrile (contains 0.1% formic acid) as eluent with a linear gradient from 10% acetonitrile to 95% acetonitrile.

Calibration was done with not branched alkan2-ones (with 3 to 16 carbon atoms) with known logP-values (measurement of logP values using retention times with linear interpolation between successive alkanones). lambda-maX-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); ...; $\delta_i$ (intensity$_i$); ...; $\delta_n$ (intensity$_n$)

---

Example IV-1: ¹H-NMR (400.1 MHz, d₆-DMSO):

δ = 8.382 (5.9); 8.375 (6.0); 7.789 (0.6); 7.780 (4.8); 7.776 (2.6); 7.768 (1.7); 7.763 (6.1); 7.759 (4.6); 7.639 (0.8); 7.636 (0.6); 7.629 (0.7); 7.621 (2.9); 7.615 (1.1); 7.607 (1.9); 7.603 (3.0); 7.600 (1.7); 7.583 (4.9); 7.580 (2.4); 7.569 (3.1); 7.565 (5.5); 7.551 (1.1); 7.547 (2.2); 7.543 (1.5); 7.158 (5.8); 7.151 (5.8); 6.442 (16.0); 6.279 (0.7); 3.354 (62.2); 3.296 (0.5); 2.892 (2.0); 2.733 (1.7); 2.515 (3.9); 2.511 (7.6); 2.507 (10.2); 2.502 (7.5); 2.498 (3.8); 1.989 (0.4)

Example IV-2: ¹H-NMR (400.0 MHz, d₆-DMSO):

δ = 8.630 (6.0); 7.768 (2.5); 7.764 (1.3); 7.757 (0.8); 7.751 (3.0); 7.747 (2.4); 7.632 (0.4); 7.614 (1.3); 7.607 (0.5); 7.600 (1.0); 7.596 (1.6); 7.592 (1.0); 7.583 (2.7); 7.564 (2.8); 7.552 (0.5); 7.547 (0.9); 7.543 (0.6); 5.796 (9.0); 3.903 (1.4); 3.846 (16.0); 3.331 (100.5); 2.512 (21.2); 2.508 (42.2); 2.503 (55.6); 2.499 (41.8); 2.330 (0.4); 0.000 (0.6)

Example IV-3: ¹H-NMR (400.0 MHz, d₆-DMSO):

δ = 7.953 (9.7); 7.765 (4.3); 7.748 (5.1); 7.744 (4.2); 7.632 (0.6); 7.623 (0.5); 7.614 (2.3); 7.608 (0.9); 7.600 (1.8); 7.597 (2.8); 7.593 (1.8); 7.584 (4.7); 7.565 (4.8); 7.552 (0.9); 7.548 (1.6); 7.543 (1.0); 5.761 (16.0); 3.903 (2.2); 3.331 (168.2); 2.672 (0.6); 2.507 (81.5); 2.503 (104.9); 2.499 (80.1); 2.334 (0.5); 2.330 (0.6); 2.325 (0.5); 0.000 (2.0)

Example IV-4: ¹H-NMR (400.1 MHz, d₆-DMSO):

δ = 8.319 (0.4); 8.155 (0.6); 7.887 (0.4); 7.881 (0.4); 7.847 (0.6); 7.841 (0.5); 7.816 (0.8); 7.810 (0.9); 7.760 (5.5); 7.758 (6.0); 7.741 (6.7); 7.737 (5.5); 7.712 (0.7); 7.708 (0.7); 7.700 (0.5); 7.691 (0.4); 7.675 (0.4); 7.669 (0.4); 7.647 (5.2); 7.641 (5.3); 7.619 (1.3); 7.615 (1.3); 7.600 (3.3); 7.593 (2.7); 7.583 (6.1); 7.577 (8.0); 7.558 (7.0); 7.541 (2.7); 7.536 (2.0); 7.524 (1.8); 7.505 (2.1); 7.487 (0.6); 7.473 (0.5); 7.456 (0.8); 7.436 (1.2); 7.418 (1.9); 7.399 (1.4); 7.372 (1.0); 7.354 (1.1); 7.347 (0.6); 7.336 (0.6); 7.329 (0.6); 7.323 (0.6); 7.309 (0.5); 7.288 (0.4); 7.244 (1.4); 6.175 (0.6); 6.160 (0.4); 6.139 (0.5); 6.131 (0.8); 6.103 (2.1); 6.066 (0.4); 6.046 (0.6); 6.041 (0.6); 6.003 (16.0); 5.974 (0.6); 5.968 (0.6); 5.961 (0.7); 5.955 (0.5); 5.874 (0.7); 5.868 (0.7); 5.559 (5.4); 5.553 (5.5); 5.372 (1.4); 5.368 (1.4); 5.331 (0.4); 5.325 (0.4); 5.262 (0.4); 5.034 (0.9); 4.875 (7.2); 4.574 (0.6); 4.557 (0.7); 4.059 (0.5); 4.041 (1.6); 4.023 (1.6); 4.006 (0.6); 3.557 (0.7); 3.349 (18.5); 3.172 (0.6); 2.968 (1.2); 2.644 (0.4); 2.632 (0.5); 2.511 (23.7); 2.507 (30.3); 2.503 (23.0); 2.334 (0.4); 2.174 (0.6); 2.145 (0.3); 1.993 (6.5); 1.903 (0.8); 1.196 (1.8); 1.178 (3.5); 1.160 (1.8)

| |
|---|
| Example IV-5: $^1$H-NMR (400.0 MHz, $d_6$-DMSO): |
| δ = 8.315 (0.3); 7.945 (9.0); 7.764 (4.9); 7.747 (5.6); 7.743 (4.7); 7.628 (0.7); 7.619 (0.6); 7.610 (2.6); 7.603 (1.1); 7.592 (3.2); 7.589 (2.1); 7.580 (5.3); 7.561 (5.3); 7.544 (1.8); 7.539 (1.2); 7.313 (2.0); 7.295 (5.6); 7.276 (5.1); 7.238 (6.9); 7.221 (3.8); 7.208 (2.1); 7.190 (2.8); 7.172 (1.0); 5.732 (16.0); 3.902 (3.0); 3.331 (221.8); 2.740 (3.1); 2.721 (4.8); 2.702 (3.4); 2.676 (0.7); 2.672 (0.8); 2.668 (0.7); 2.507 (101.2); 2.503 (130.0); 2.499 (99.9); 2.448 (3.4); 2.431 (7.1); 2.413 (3.6); 2.334 (0.6); 2.330 (0.7); 2.325 (0.6); 1.882 (1.0); 1.865 (3.0); 1.845 (3.8); 1.827 (2.8); 1.809 (0.8); 1.231 (0.5); 0.000 (2.4) |
| Example IV-6: $^1$H-NMR (400.0 MHz, $d_6$-DMSO): |
| δ = 7.918 (8.9); 7.765 (3.4); 7.763 (4.3); 7.759 (2.2); 7.751 (1.5); 7.746 (5.2); 7.742 (4.1); 7.629 (0.6); 7.626 (0.4); 7.620 (0.4); 7.611 (2.3); 7.604 (0.8); 7.597 (1.8); 7.594 (2.9); 7.589 (1.7); 7.581 (4.8); 7.566 (2.3); 7.563 (4.8); 7.550 (0.8); 7.545 (1.6); 7.541 (1.0); 5.724 (16.0); 3.903 (2.2); 3.333 (198.5); 3.292 (0.3); 2.677 (0.4); 2.672 (0.5); 2.668 (0.4); 2.525 (1.4); 2.512 (32.7); 2.508 (64.6); 2.503 (84.2); 2.499 (61.9); 2.494 (31.2); 2.428 (3.8); 2.411 (8.1); 2.393 (4.2); 2.335 (0.4); 2.330 (0.5); 2.326 (0.4); 1.606 (0.5); 1.588 (2.3); 1.570 (4.7); 1.552 (2.6); 1.516 (0.6); 1.011 (7.3); 0.993 (14.6); 0.974 (6.5); 0.000 (1.2) |
| Example IV-7: $^1$H-NMR (400.0 MHz, $d_6$-DMSO): |
| δ = 7.953 (1.1); 7.911 (9.2); 7.762 (4.6); 7.745 (5.6); 7.741 (4.3); 7.629 (0.7); 7.620 (0.5); 7.611 (2.5); 7.604 (0.9); 7.597 (2.1); 7.593 (3.1); 7.589 (1.8); 7.581 (5.1); 7.562 (5.2); 7.545 (1.7); 7.541 (1.0); 5.761 (1.7); 5.722 (16.0); 3.903 (2.5); 3.329 (126.9); 2.676 (0.5); 2.672 (0.6); 2.668 (0.5); 2.507 (78.5); 2.503 (101.0); 2.499 (75.1); 2.452 (3.6); 2.435 (7.5); 2.417 (4.0); 2.334 (0.4); 2.330 (0.6); 2.325 (0.4); 1.561 (0.6); 1.544 (2.0); 1.537 (1.0); 1.525 (3.1); 1.520 (1.8); 1.507 (3.1); 1.490 (1.2); 1.469 (0.7); 1.451 (2.1); 1.433 (3.0); 1.413 (3.0); 1.396 (1.5); 1.379 (0.4); 1.337 (1.0); 1.233 (1.4); 1.225 (1.4); 0.926 (7.1); 0.907 (13.4); 0.889 (5.9); 0.000 (2.2) |
| Example IV-8: $^1$H-NMR (400.0 MHz, $d_6$-DMSO): |
| δ = 7.894 (9.9); 7.757 (4.5); 7.740 (5.3); 7.736 (4.3); 7.628 (0.7); 7.625 (0.5); 7.619 (0.5); 7.610 (2.4); 7.603 (0.9); 7.596 (1.9); 7.592 (3.0); 7.588 (1.8); 7.580 (4.9); 7.561 (4.9); 7.548 (1.9); 7.544 (1.6); 7.539 (1.0); 5.710 (16.0); 3.902 (2.4); 3.335 (256.3); 2.677 (0.5); 2.672 (0.6); 2.668 (0.5); 2.508 (80.7); 2.503 (103.9); 2.499 (77.4); 2.334 (0.4); 2.330 (0.6); 2.325 (0.5); 1.591 (0.5); 1.578 (1.1); 1.570 (1.1); 1.566 (0.8); 1.557 (2.2); 1.549 (0.8); 1.545 (1.2); 1.537 (1.2); 1.524 (0.6); 0.927 (1.1); 0.916 (3.2); 0.910 (4.1); 0.900 (2.0); 0.896 (3.3); 0.889 (3.6); 0.880 (1.5); 0.767 (1.6); 0.758 (4.2); 0.751 (3.8); 0.746 (4.1); 0.739 (3.8); 0.728 (1.1); 0.000 (1.3) |
| Example IV-9: $^1$H-NMR (400.0 MHz, $d_6$-DMSO): |
| δ = 7.907 (9.8); 7.762 (4.7); 7.745 (5.5); 7.741 (4.6); 7.629 (0.7); 7.624 (0.8); 7.620 (0.6); 7.611 (2.5); 7.604 (1.0); 7.597 (2.0); 7.593 (3.1); 7.589 (1.9); 7.581 (5.1); 7.562 (5.2); 7.549 (0.9); 7.545 (1.7); 7.540 (1.1); 5.761 (0.3); 5.722 (16.0); 3.902 (3.0); 3.333 (252.5); 2.672 (1.3); 2.668 (1.5); 2.662 (1.1); 2.650 (1.4); 2.641 (1.6); 2.628 (0.8); 2.618 (1.8); 2.507 (84.5); 2.503 (111.2); 2.499 (84.6); 2.334 (0.5); 2.330 (0.6); 2.326 (0.5); 1.837 (1.5); 1.827 (1.6); 1.812 (1.8); 1.804 (1.7); 1.704 (0.9); 1.681 (1.9); 1.668 (2.2); 1.660 (1.9); 1.511 (1.7); 1.504 (1.7); 1.480 (2.3); 1.456 (1.9); 1.433 (0.8); 1.425 (0.8); 1.380 (0.7); 1.357 (1.8); 1.350 (1.5); 1.332 (4.0); 1.310 (2.3); 1.234 (0.4); 0.000 (2.2) |
| Example IV-10: $^1$H-NMR (400.0 MHz, $d_6$-DMSO): |
| δ = 7.911 (9.3); 7.762 (4.5); 7.758 (2.4); 7.751 (1.4); 7.745 (5.2); 7.741 (4.2); 7.629 (0.7); 7.626 (0.5); 7.620 (0.5); 7.611 (2.4); 7.604 (0.9); 7.597 (1.8); 7.593 (3.0); 7.589 (1.7); 7.581 (5.0); 7.566 (2.3); 7.562 (4.8); 7.549 (0.8); 7.545 (1.6); 7.540 (1.0); 5.723 (16.0); 3.902 (2.6); 3.376 (0.5); 3.333 (185.6); 2.676 (0.4); 2.672 (0.5); 2.668 (0.4); 2.512 (34.4); 2.508 (69.4); 2.503 (92.2); 2.499 (69.2); 2.494 (35.7); 2.443 (3.4); 2.426 (7.3); 2.408 (3.7); 2.334 (0.4); 2.330 (0.6); 2.326 (0.4); 1.578 (0.6); 1.561 (1.9); 1.543 (2.9); 1.524 (2.6); 1.506 (1.0); 1.422 (0.7); 1.407 (1.6); 1.399 (1.4); 1.389 (1.9); 1.384 (2.0); 1.379 (1.5); 1.374 (1.4); 1.367 (2.0); 1.351 (1.6); 1.343 (2.0); 1.327 (2.4); 1.308 (2.1); 1.288 (1.1); 1.271 (0.4); 0.902 (6.3); 0.884 (11.9); 0.866 (4.8); 0.000 (1.9) |
| Example V-1: $^1$H-NMR (400.1 MHz, $d_6$-DMSO): |
| δ = 11.244 (1.8); 10.189 (0.4); 9.631 (0.3); 9.581 (12.2); 9.133 (0.4); 8.141 (2.4); 8.007 (0.8); 8.001 (0.8); 7.983 (0.8); 7.977 (0.8); 7.771 (0.4); 7.765 (0.4); 7.739 (0.4); 7.648 (0.7); 7.639 (0.6); 7.614 (2.5); 7.604 (6.1); 7.600 (7.4); 7.588 (6.9); 7.580 (6.9); 7.573 (7.4); 7.567 (7.1); 7.531 (0.4); 7.522 (0.4); 7.459 (0.9); 7.428 (6.1); 7.421 (12.6); 7.417 (11.9); 7.407 (6.6); 7.404 (6.6); 7.390 (3.3); 7.365 (0.5); 7.336 (0.4); 7.325 (0.4); 7.297 (0.3); 6.347 (0.5); 6.342 (0.7); 6.337 (0.4); 6.151 (0.6); 6.132 (0.8); 6.126 (0.8); 6.041 (2.0); 6.003 (0.5); 5.949 (2.1); 5.915 (1.3); 5.882 (1.6); 5.859 (1.3); 5.834 (8.8); 5.786 (0.3); 5.764 (0.5); 5.737 (16.0); 5.715 (0.7); 5.511 (6.7); 5.505 (6.5); 4.754 (10.3); 4.060 (0.9); 4.042 (2.7); 4.024 (2.7); 4.006 (0.9); 3.353 (157.0); 2.962 (1.2); 2.676 (0.4); 2.643 (0.5); 2.630 (0.5); 2.511 (45.5); 2.507 (59.7); 2.503 (44.8); 2.334 (0.5); 1.994 (11.4); 1.770 (1.1); 1.736 (1.1); 1.197 (3.0); 1.179 (5.9); 1.161 (3.0); 1.050 (0.4); 1.035 (0.4) |
| Example V-2: $^1$H-NMR (400.0 MHz, $d_6$-DMSO): |
| δ = 9.594 (5.0); 8.315 (0.4); 7.883 (13.1); 7.618 (3.5); 7.614 (4.5); 7.609 (2.5); 7.607 (2.5); 7.601 (3.9); 7.594 (5.1); 7.458 (0.4); 7.442 (2.1); 7.434 (8.4); 7.431 (8.0); 7.416 (4.5); 7.407 (1.1); 7.403 (1.2); 7.398 (0.5); 7.394 (0.7); 5.957 (4.1); 5.464 (16.0); 5.413 (0.4); 3.902 (2.9); 3.331 (263.4); 2.676 (0.6); 2.671 (0.8); 2.667 (0.6); 2.541 (0.5); 2.507 (105.8); 2.502 (137.4); 2.498 (102.4); 2.333 (0.6); 2.329 (0.8); 2.325 (0.6); 0.000 (2.4) |
| Example V-3: $^1$H-NMR (400.0 MHz, $d_6$-DMSO): |
| δ = 9.590 (4.0); 8.314 (0.4); 7.852 (9.8); 7.616 (3.1); 7.612 (4.0); 7.607 (2.1); 7.604 (2.2); 7.599 (3.3); 7.592 (4.5); 7.443 (1.0); 7.438 (1.9); 7.430 (7.4); 7.427 (6.9); 7.420 (2.5); 7.412 (3.9); 7.404 (1.0); 7.394 (0.4); 7.390 (0.5); 5.944 (3.3); 5.427 (13.3); 3.902 (3.4); 3.335 (279.3); 2.676 (0.5); 2.671 (0.7); 2.667 (0.5); 2.542 (0.4); 2.525 (1.9); 2.511 (43.5); 2.507 (87.3); 2.502 (115.0); 2.498 (84.7); 2.493 (42.4); 2.422 (4.0); 2.404 (8.5); 2.387 (4.3); 2.334 (0.5); 2.329 (0.7); 2.325 (0.5); 1.604 (0.5); 1.586 (2.5); 1.568 (5.1); 1.550 (5.2); 1.532 (2.7); 1.514 (0.6); 1.011 (8.0); 0.993 (16.0); 0.974 (7.1); 0.000 (0.8) |
| Example V-4: $^1$H-NMR (400.0 MHz, $d_6$-DMSO): |
| δ = 9.587 (5.2); 8.315 (0.4); 7.845 (11.2); 7.616 (3.4); 7.612 (4.4); 7.604 (2.4); 7.598 (3.7); 7.592 (5.0); 7.454 (0.3); 7.442 (1.1); 7.437 (2.1); 7.430 (8.3); 7.426 (7.6); 7.420 (2.8); 7.412 (4.4); 7.403 (1.1); 7.399 (1.2); 7.394 (0.5); 7.389 (0.6); 5.943 (4.2); 5.426 (14.7); 3.902 (3.8); 3.330 (191.0); 2.675 (0.5); 2.671 (0.7); 2.667 (0.5); 2.541 (0.3); 2.524 (1.9); 2.511 (46.6); 2.506 (93.8); 2.502 (123.9); 2.497 (92.0); 2.493 (46.6); 2.446 (3.9); 2.429 (8.4); 2.411 (4.4); 2.333 (0.6); 2.329 (0.8); 2.324 (0.6); 1.557 (0.6); 1.542 (2.2); 1.535 (1.1); 1.523 (3.4); 1.517 (2.1); 1.505 (3.5); 1.488 (1.4); 1.470 (0.8); 1.459 (0.8); 1.452 (2.5); 1.440 (1.5); 1.434 (3.4); 1.421 (1.5); 1.414 (3.0); 1.396 (1.7); 1.379 (0.4); 0.927 (8.3); 0.908 (16.0); 0.890 (6.9); 0.000 (3.0) |

-continued

Example V-5: $^1$H-NMR (400.0 MHz, d$_6$-DMSO):

δ = 9.587 (8.0); 8.315 (0.4); 7.841 (13.1); 7.616 (3.8); 7.612 (4.9); 7.606 (2.7); 7.604 (2.8); 7.598 (4.2); 7.592 (5.6); 7.577 (0.4); 7.569 (0.4); 7.471 (0.4); 7.468 (0.4); 7.454 (0.5); 7.437 (2.4); 7.430 (9.3); 7.426 (8.7); 7.419 (3.3); 7.412 (4.9); 7.403 (1.2); 7.399 (1.3); 7.394 (0.5); 7.389 (0.7); 5.943 (5.9); 5.426 (16.0); 5.409 (0.9); 3.902 (6.5); 3.331 (320.5); 3.175 (0.9); 3.163 (0.8); 2.676 (1.1); 2.671 (1.4); 2.667 (1.5); 2.654 (1.2); 2.645 (1.7); 2.635 (1.2); 2.622 (1.0); 2.614 (0.5); 2.541 (0.5); 2.511 (58.8); 2.507 (115.7); 2.502 (150.9); 2.498 (112.5); 2.333 (0.6); 2.329 (0.9); 2.324 (0.7); 1.834 (1.8); 1.824 (2.0); 1.810 (2.2); 1.802 (2.0); 1.682 (2.2); 1.676 (2.2); 1.669 (2.6); 1.660 (2.2); 1.510 (1.9); 1.502 (2.0); 1.477 (2.7); 1.454 (2.2); 1.430 (0.9); 1.423 (1.0); 1.381 (0.8); 1.357 (2.1); 1.332 (5.0); 1.311 (2.7); 0.000 (2.7)

Example V-6: $^1$H-NMR (400.0 MHz, d$_6$-DMSO):

δ = 9.588 (5.7); 8.315 (0.4); 7.845 (11.4); 7.616 (3.8); 7.612 (5.0); 7.603 (3.0); 7.598 (4.4); 7.592 (5.6); 7.454 (0.4); 7.437 (2.4); 7.430 (9.3); 7.426 (9.0); 7.420 (3.6); 7.412 (5.0); 7.403 (1.3); 7.399 (1.4); 7.389 (0.7); 5.943 (5.0); 5.426 (16.0); 3.902 (4.4); 3.332 (242.8); 3.174 (1.1); 3.163 (1.0); 2.675 (0.6); 2.671 (0.8); 2.667 (0.7); 2.541 (0.6); 2.506 (109.6); 2.502 (142.5); 2.498 (108.2); 2.438 (4.3); 2.420 (9.1); 2.403 (4.6); 2.333 (0.6); 2.329 (0.8); 2.324 (0.6); 1.576 (0.8); 1.559 (2.5); 1.541 (4.0); 1.522 (3.5); 1.504 (1.3); 1.423 (0.9); 1.408 (2.2); 1.400 (2.0); 1.390 (2.6); 1.385 (2.8); 1.375 (2.0); 1.368 (2.8); 1.352 (2.2); 1.345 (2.8); 1.329 (3.3); 1.310 (2.8); 1.290 (1.5); 1.273 (0.5); 0.904 (8.2); 0.886 (15.3); 0.868 (6.2); 0.000 (2.6)

Example VI-1: $^1$H-NMR (400.1 MHz, d$_6$-DMSO):

δ = 8.336 (4.4); 8.330 (4.4); 8.282 (0.3); 7.575 (2.1); 7.571 (2.8); 7.556 (4.3); 7.552 (5.3); 7.540 (2.5); 7.529 (3.0); 7.521 (5.8); 7.509 (1.8); 7.502 (3.2); 7.491 (1.0); 7.487 (1.3); 7.481 (0.9); 7.467 (0.4); 7.138 (4.6); 7.131 (4.6); 6.794 (0.6); 6.729 (0.4); 6.286 (10.1); 6.156 (0.5); 4.367 (0.3); 4.059 (0.9); 4.041 (2.6); 4.023 (2.6); 4.005 (0.9); 3.792 (0.4); 3.776 (0.5); 3.761 (0.4); 3.353 (53.7); 3.297 (1.6); 3.196 (0.4); 2.958 (16.0); 2.895 (0.3); 2.511 (24.2); 2.507 (31.8); 2.502 (23.6); 1.993 (11.2); 1.196 (3.0); 1.178 (5.9); 1.160 (3.0); 1.048 (10.7); 1.033 (10.7)

Example VI-2: $^1$H-NMR (300.2 MHz, d$_6$-DMSO):

δ = 7.941 (5.6); 7.533 (10.5); 6.832 (2.7); 5.596 (10.5); 3.361 (20.4); 3.184 (0.4); 3.152 (16.0); 2.521 (8.0)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

BIOLOGY

Example A: In Vivo Preventive Test on *Alternaria brassicae* (Leaf Spot on Radish)

The tested active ingredients are prepared by homogenization in a mixture of acetone/Dimethyl sulfoxide/Tween®, and then diluted with water to obtain the desired active material concentration.

The young plants of radish are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Alternaria brassicae* spores. The contaminated radish plants are incubated for 6 days at 20° C. and at 100% relative humidity.

The test is evaluated 6 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Example | % efficacy |
|---------|------------|
| 10      | 97         |

Example B: In Vivo Preventive Test on *Botrytis cinerea* (Grey Mould)

The tested active ingredients are prepared by homogenization in a mixture of acetone/Dimethyl sulfoxide/Tween®, and then diluted with water to obtain the desired active material concentration.

The young plants of gherkin are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Example | % efficacy |
|---|---|
| 15 | 73 |

Example C: In Vivo Preventive Test on *Phytophthora infestans* (Tomato Late Blight)

The tested active ingredients are prepared by homogenization in a mixture of acetone/Dimethyl sulfoxide/Tween®, and then diluted with water to obtain the desired active material concentration.

The young plants of tomato are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Phytophthora infestans* spores. The contaminated tomato plants are incubated for 5 days at 16-18° C. and at 100% relative humidity.

The test is evaluated 5 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Example | % efficacy |
|---|---|
| 1 | 98 |
| 4 | 100 |
| 5 | 100 |
| 6 | 100 |
| 9 | 79 |
| 10 | 100 |
| 11 | 100 |
| 12 | 100 |
| 13 | 95 |
| 14 | 74 |
| 15 | 100 |
| 16 | 80 |
| 17 | 100 |
| 18 | 99 |
| 19 | 98 |
| 20 | 90 |
| 21 | 100 |
| 22 | 100 |
| 23 | 99 |
| 24 | 98 |
| 27 | 92 |
| 28 | 73 |
| 29 | 83 |
| 30 | 97 |
| 31 | 94 |
| 34 | 100 |
| 35 | 93 |
| 36 | 99 |
| 37 | 100 |
| 38 | 100 |
| 39 | 88 |
| 40 | 100 |

Example D: In Vivo Preventive Test on *Puccinia recondita* (Brown Rust on Wheat)

The tested active ingredients are prepared by homogenization in a mixture of acetone/Dimethyl sulfoxide/Tween®, and then diluted with water to obtain the desired active material concentration.

The young plants of wheat are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Example | % efficacy |
|---|---|
| 20 | 78 |

Example E: In Vivo Preventive Test on *Pyrenophora teres* (Net Blotch on Barley)

The tested active ingredients are prepared by homogenization in a mixture of acetone/Dimethyl sulfoxide/Tween®, and then diluted with water to obtain the desired active material concentration.

The young plants of barley are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Pyrenophora teres* spores. The contaminated barley plants are incubated for 48 hours at 20° C. and at 100% relative humidity and then for 12 days at 20° C. and at 70-80% relative humidity.

The test is evaluated 14 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Example | % efficacy |
| --- | --- |
| 18 | 71 |
| 16 | 71 |
| 6 | 80 |

Example F: In Vivo Preventive Test on *Pyricularia oryzae* (Rice Blast)

The tested active ingredients are prepared by homogenization in a mixture of acetone/Dimethyl sulfoxide/Tween®, and then diluted with water to obtain the desired active material concentration.

The young plants of rice are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Pyricularia oryzae* spores. The contaminated rice plants are incubated at 25° C. and at 80% relative humidity.

The test is evaluated 6 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Example | % efficacy |
| --- | --- |
| 13 | 79 |

Example G: In Vivo Preventive Test on *Septoria tritici* (Leaf Spot on Wheat)

The tested active ingredients are prepared by homogenization in a mixture of acetone/Dimethyl sulfoxide/Tween®, and then diluted with water to obtain the desired active material concentration.

The young plants of wheat are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Example | % efficacy |
| --- | --- |
| 5 | 86 |
| 16 | 79 |
| 29 | 79 |
| 34 | 86 |

Example H: In Vivo Preventive Test on *Uromyces appendiculatus* (Bean Rust)

The tested active ingredients are prepared by homogenization in a mixture of acetone/Dimethyl sulfoxide/Tween®, and then diluted with water to obtain the desired active material concentration.

The young plants of bean are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy of at least 70% at a concentration of 500 ppm of active ingredient.

| Example | % efficacy |
| --- | --- |
| 18 | 72 |
| 20 | 81 |

Example I: *Phytophthora* Test (Tomato)/Preventive

| | |
| --- | --- |
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 500 ppm of active ingredient.

| Example | Eff. % |
|---|---|
| 7 | 100 |

Example J: *Plasmopara* Test (Grapevines)/Preventive

| | |
|---|---|
| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the untreated control, while an efficacy of 100% means that no disease is observed.

In this test the following compounds according to the invention showed efficacy of 70% or even higher at a concentration of 10 ppm of active ingredient.

| Example | Eff. % |
|---|---|
| 7 | 85 |
| 15 | 75 |
| 6 | 99 |
| 17 | 84 |
| 22 | 85 |
| 27 | 99 |
| 38 | 96 |
| 40 | 99 |

CHEMISTRY

The following examples illustrate in a non-limiting manner the preparation and efficacy of the compounds of formula (I) according to the invention.

Preparation Example 1: 2-methyl-3-[(Z)-{[(3-nitro-1H-pyrazol-1-yl)methoxy]imino}(phenyl)methyl]-1,2,4-oxadiazol-5(2H)-one (compound 2)

Step 1: Preparation of (2Z)-{[(3-nitro-1H-pyrazol-1-yl)methoxy]imino}(phenyl)acetonitrile (Compound IV-1) According to Process P1

To a solution of (sodium {[(Z)-cyano(phenyl)methylene]amino}oxidanide (1.84 g, 10.95 mmol, 1 eq.) in 50 ml of acetonitrile and 5 ml DMF was added N-chloromethyl-3-nitropyrazole (obtained by standard chlorination of the N-chloromethyl-3-nitropyrazole described in WO201113045) (1.77 g, 10.95 mmol, 1 eq.) followed by potassium iodide (90.9 mg, 0.547 mmol, 0.05 eq.). The reaction was stirred 3 hours at room temperature. The solvent was then evaporated and the residue dissolved in EtOAc (50 ml). The organic layer was washed with $H_2O$ and brine and dried over $MgSO_4$ then concentrated. (2Z)-{[(3-nitro-1H-pyrazol-1-yl)methoxy]imino}(phenyl)acetonitrile (2.89 g, 96% yield) was obtained as a white solid.

Step 2: Preparation of (2Z)—N-hydroxy-N-methyl-2-{[(3-nitro-1H-pyrazol-1-yl)methoxy]imino}-2-phenylethanimidamide (Compound VI-1) According to Process P2

To a solution of (2Z)-{[(3-nitro-1H-pyrazol-1-yl)methoxy]imino}(phenyl)acetonitrile (100 mg, 0.369 mmol, 1 eq.) and potassium carbonate (203 mg, 1.48 mmol, 4 eq) in 2-propanol/water (4 ml/1 ml), was added N-methylhydroxylamine hydrochloride (123 mg, 1.48 mmol, 4 eq.). The reaction was heated under stirring to 80° C. for 2 h and the solvent was evaporated to $\frac{3}{4}^{th}$. The residue was extracted with EtOAc and washed with water. The organics were combined, dried over $MgSO_4$ and concentrated to give (2Z)—N-hydroxy-N-methyl-2-{[(3-nitro-1H-pyrazol-1-yl)methoxy]imino}-2-phenylethanimidamide (110 mg, 89% yield), which was used in the next step without further purification.

Step 3: Preparation of 2-methyl-3-[(Z)-{[(3-nitro-1H-pyrazol-1-yl)methoxy]imino}(phenyl)methyl]-1,2,4-oxadiazol-5(2H)-one (Compound 2) According to Process P2

To a solution of (2Z)—N-hydroxy-N-methyl-2-{[(3-nitro-1H-pyrazol-1-yl)methoxy]imino}-2-phenylethanimidamide (117 mg, 0.369 mmol, 1 eq.) in DMF (2 ml) was added 1,1'-carbonyldiimidazole (65.8 mg, 0.406 mmol, 1.1 eq.) and stirring at room temperature was allowed for 1 h. The reaction was quenched by addition of water and extracted with EtOAc (3×50 ml). The organics were combined, washed with aq. sat. NaCl, dried over $MgSO_4$ and concentrated to give 2-methyl-3-[(Z)-{[(3-nitro-1H-pyrazol-1-yl)methoxy]imino}(phenyl)methyl]-1,2,4-oxadiazol-5(2H)-one (123 mg, 92% yield).

Preparation Example 2: 3-[(Z)-{[(3-amino-1H-pyrazol-1-yl)methoxy]imino}(phenyl)methyl]-2-methyl-1,2,4-oxadiazol-5(2H)-one (compound 8)

A solution of 2-methyl-3-[(Z)-{[(3-nitro-1H-pyrazol-1-yl)methoxy]imino}(phenyl)methyl]-1,2,4-oxadiazol-5(2H)-one (100 mg, 0.29 mmol, 1 eq) in ethyl acetate (20 mL) was hydrogenated with H-Cube over a Pt/C cartridge at 1 mL/min at 50° C. under full H2. The solvent was then evaporated to afford 3-[(Z)-{[(3-amino-1H-pyrazol-1-yl)methoxy]imino}(phenyl)methyl]-2-methyl-1,2,4-oxadiazol-5(2H)-one (80 mg, 70% yield, 80% purity).

Preparation Example 3: pentyl {1-[({[(Z)-(2-methyl-5-oxo-2,5-dihydro-1,2,4-oxadiazol-3-yl)(phenyl)methylene]amino}oxy)methyl]-1H-pyrazol-3-yl}carbamate (compound 7) according to Process P3

To a solution of 3-[(Z)-{[(3-amino-1H-pyrazol-1-yl)methoxy]imino}(phenyl)methyl]-2-methyl-1,2,4-oxadiazol-5(2H)-one (80 mg, 0.255 mmol, 1 eq) in pyridine (2 ml) was added pentylcarbamoyl chloride (76.7 mg, 0.509 mmol, 2 eq.) and stirring was allowed overnight. The reaction was quenched by addition of 1M HCl and extracted with ethyl acetate. The organics were combined, washed with 1N NaOH and dried over MgSO₄. After concentration, the residue was purified by chromatography on silica gel to give pentyl {1-[({[(Z)-(2-methyl-5-oxo-2,5-dihydro-1,2,4-oxadiazol-3-yl)(phenyl)methylene]amino}oxy)methyl]-1H-pyrazol-3-yl}carbamate (86 mg, 65% yield).

Preparation Example 4: 3-[{[(4-bromo-1,3-thiazol-2-yl)methoxy]imino}(phenyl)methyl]-4-methyl-1,2,4-oxadiazol-5(4H)-one (compound 3) according to process P1

Step 1: Preparation of {[(4-bromo-1,3-thiazol-2-yl)methoxy]imino}(phenyl)acetonitrile (compound IV-1) according to process P1

To the stirred solution of hydroxyiminophenylacetonitrile (6 g, 1 eq), cesium carbonate (20 g, 1.5 eq) and potassium iodide (0.68 g, 0.1 eq) in 80 ml of ACN and 10 ml of DMF, 4-bromo-2-(bromomethyl)-1,3-thiazole (10.5 g, 1 eq) prepared according to Synthesis, 2009, 1979 was added at RT. The reaction mixture was stirred overnight at room temperature. After work up and purification by chromatography on silica gel 10.5 g (78% yield) of {[(4-bromo-1,3-thiazol-2-yl)methoxy]imino}(phenyl)acetonitrile (compound IV-1) was obtained as an orange solid.

Step 2

To the stirred solution of {[(4-bromo-1,3-thiazol-2-yl)methoxy]imino}(phenyl)acetonitrile (100 mg, 1 eq) in 1 ml of isopropanol, potassium carbonate (128 mg, 3 eq) and hydroxylamine hydrochloride (63 mg, 3 eq, in 1 ml of water) were added at RT and refluxed for 3 h. After work up the obtained crude was taken in 1 ml of DMF, carbonyldiimidazole (50 mg, 1 eq) was added at and stirred for 30 min at RT, then reaction mixture was heated to 80° C. After work up without any further purification the obtained crude 3-[{[(4-bromo-1,3-thiazol-2-yl)methoxy]imino}(phenyl) methyl]-1,2,4-oxadiazol-5(4H)-one was directly used for next step.

Step 3

To the stirred solution of 3-[{[(4-bromo-1,3-thiazol-2-yl)methoxy]imino}(phenyl)methyl]-1,2,4-oxadiazol-5(4H)-one (50 mg, 1 eq) in 1 ml of acetonitrile and 0.5 ml of DMF, MeI (37 mg, 2 eq) and potassium carbonate (36 mg, 2 eq) were added at RT and stirred for 12 h at same temperature. After work up without any further purification 50 mg of crude 3-[{[(4-bromo-1,3-thiazol-2-yl)methoxy]imino}(phenyl)methyl]-4-methyl-1,2,4-oxadiazol-5(4H)-one (compound 3) was obtained.

Preparation Example 5: 3-[(Z)-{[(4-bromo-1,3-thiazol-2-yl)methoxy]imino}(phenyl)methyl]-2-methyl-1,2,4-oxadiazol-5(2H)-one (compound 14) according to process P2

Step 1: Preparation of (2Z)-2-{[(4-bromo-1,3-thiazol-2yl)methoxy]imino}-N-hydroxy-N-methyl-2-phenylethanimidamide (Compound VI-2) According to Process P2

To a solution of {[(4-bromo-1,3-thiazol-2-yl)methoxy]imino}(phenyl)acetonitrile (compound IV-1) (5.5 g, 17 mmol, 1 eq.) in 2-propanol/water (100 ml/10 ml), was added potassium carbonate (4.7 g, 34 mmol, 2 eq) and N-methylhydroxylamine hydrochloride (2.85 g, 34 mmol, 2 eq.). The reaction was heated under stirring to 80° C. for 2 h. The reaction mixture was poured onto 250 mL of water and extracted twice with EtOAc. The combined organic layers were washed with brine, dried over MgSO₄ and concentrated. The residue was purified by chromatography on silica gel to give ((2Z)-2-{[(4-bromo-1,3-thiazol-2-yl)methoxy]imino}-N-hydroxy-N-methyl-2-phenylethanimidamide (compound VI-2) (3.7 g, 56% yield) as a yellow solid.

Step 2

To a solution of (2Z)-2-{[(4-bromo-1,3-thiazol-2-yl)methoxy]imino}-N-hydroxy-N-methyl-2-phenylethanimidamide (3.2 g, 8.66 mmol, 1 eq.) in acetonitrile (80 ml) was added 1,1'-carbonyldiimidazole (2.8 g, 17.3 mmol, 2 eq.) and stirring at room temperature was allowed for 3 h. The reaction was quenched by addition of water (500 mL) and extracted with EtOAc (2*500 ml). The organics were combined, washed with aq. sat. NaCl, dried over MgSO₄ and concentrated. The residue was purified by chromatography on silica gel to give 3-[(Z)-{[(4-bromo-1,3-thiazol-2-yl)methoxy]imino}(phenyl)methyl]-2-methyl-1,2,4-oxadiazol-5(2H)-one (compound 14) (3.6 g, 77% yield).

Preparation Example 6: 3-[(Z)-({[4-(cyclopropylethynyl)-1,3-thiazol-2-yl]methoxy}imino)(phenyl)methyl]-2-methyl-1,2,4-oxadiazol-5(2H)-one (compound 4) according to process P4

To a solution of 3-[(Z)-{[(4-bromo-1,3-thiazol-2-yl)methoxy]imino}(phenyl)methyl]-2-methyl-1,2,4-oxadiazol-5(2H)-one (compound 14) (200 mg, 0.5 mmol, 1 eq.) in THF (2 mL) were added under argon tetrakis(triphenylphosphine) palladium (0) (58 mg, 0.05 mmol, 0.1 eq.), copper (I) iodide (14.5 mg, 0.076 mmol, 0.15 eq.), diisopropylethylamine (0.35 mL, 2 mmol, 4 eq.) and ethynylcyclopropane (100 mg, 1.5 mmol, 3 eq.). The mixture was stirred for 24 h at room temperature, diluted with ethyl acetate, filtered over celite and evaporated. The residue was purified by chromatography on silica gel to give 3-[(Z)-({[4-(cyclopropylethynyl)-1,3-thiazol-2-yl]methoxy}imino)(phenyl)methyl]-2-methyl-1,2,4-oxadiazol-5(2H)-one (compound 4) (140 mg, 69% yield).

The invention claimed is:
1. A compound of formula (I)

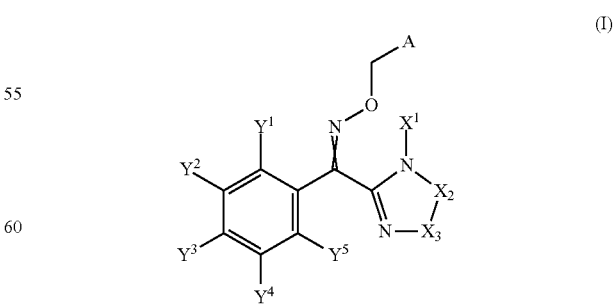

and/or a salt, N-oxide, metallic complex, and/or metalloidic complex thereof and/or an (E) and/or (Z) isomer and/or a mixture thereof, wherein X$^1$ represents a hydrogen atom, substituted or non-substituted C$_1$-C$_8$-alkyl, substituted or non-substituted C$_3$-C$_8$-cycloalkyl, or a substituted or non-substituted C$_2$-C$_8$-alkenyl;

X$^2$ and X$^3$ represent O or C=O, provided that X$^2$ represents O when X$^3$ is C=O and X$^2$ represents C=O when X$^3$ is O;

A is

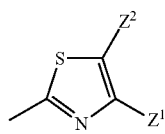

A$^1$ wherein

Z$^1$ represents a hydrogen atom, a halogen atom, a nitro group, an amino group, a carbamoyl group, substituted or non-substituted C$_1$-C$_8$-alkyl, substituted or non-substituted C$_3$-C$_8$-cycloalkyl, substituted or non-substituted C$_2$-C$_8$-alkenyl, substituted or non-substituted C$_2$-C$_8$-alkynyl, substituted or non-substituted aryl-C$_2$-C$_8$-alkynyl, substituted or non-substituted C$_3$-C$_8$-cycoalkyl-C$_2$-C$_8$-alkynyl, substituted or non-substituted N—C$_1$-C$_8$-alkyl-carbamoyl, substituted or non-substituted N—C$_3$-C$_8$-cycloalkyl-carbamoyl, substituted or non-substituted N-aryl-carbamoyl, or a group of formula QC(=U)NR$^a$— wherein

Q represents a hydrogen atom, substituted or non-substituted C$_1$-C$_8$-alkyl, substituted or non-substituted C$_3$-C$_8$-cycloalkyl, a substituted or non-substituted C$_2$-C$_8$-alkenyl, substituted or non-substituted C$_1$-C$_8$-alkoxy, substituted or non-substituted C$_2$-C$_8$-alkenyloxy, substituted or non-substituted C$_2$-C$_8$-alkynyloxy, substituted or non-substituted aryl, substituted or non-substituted heterocyclyl, substituted or non-substituted C$_5$-C$_{12}$-benzofused heterocyclyl, substituted or non-substituted aryl-C$_1$-C$_8$-alkyl, substituted or non-substituted aryloxy-C$_1$-C$_8$-alkyl, or substituted or non-substituted C$_1$-C$_8$-alkoxy-C$_1$-C$_8$-alkyl, wherein optional substituents for Q are selected from the group consisting of a halogen atom, a cyano group, a C$_1$-C$_8$-alkyl group, and a C$_1$-C$_8$-alkoxy group;

U represents a oxygen atom; and

R$^a$ represents a hydrogen atom, a hydroxy group, substituted or non-substituted C$_1$-C$_8$-alkyl, substituted or non-substituted C$_3$-C$_8$-cycloalkyl, or substituted or non-substituted C$_1$-C$_8$-alkoxy;

Z$^2$ represents a hydrogen atom, a halogen atom, substituted or non-substituted C$_1$-C$_8$-alkyl, substituted or non-substituted C$_3$-C$_8$-cycloalkyl, substituted or non-substituted C$_2$-C$_8$-alkenyl, substituted or non-substituted C$_2$-C$_8$-alkynyl, or substituted or non-substituted C$_1$-C$_8$-alkoxy; and Y$^1$ to Y$^5$ independently represent a hydrogen atom, a halogen atom, C$_1$-C$_8$-alkyl, C$_3$-C$_8$-cycloalkyl, C$_1$-C$_8$-halogenoalkyl having 1 to 5 halogen atoms, or C$_1$-C$_8$-alkoxy.

2. A compound according to claim 1 wherein X$^1$ represents a hydrogen atom, a methyl group, an ethyl group, an n-propyl group, an isopropyl group or a cyclopropyl group.

3. A compound according to claim 1 wherein Z$^1$ represents a halogen atom, a nitro group, a carboxylic acid, an amino group, substituted or non-substituted C$_2$-C$_8$-alkynyl, or a group of formula QC(=U)NR$^a$.

4. A compound according to claim 1 wherein R$^a$ represents a hydrogen atom.

5. A compound according to claim 1 wherein Q represents a substituted or non-substituted C$_4$-C$_8$-alkyl, substituted or non-substituted C$_3$-C$_8$-cyclo-alkyl, substituted or non-substituted C$_4$-C$_8$-alkenyl, substituted or non-substituted C$_4$-C$_8$-alkoxy, substituted or non-substituted C$_4$-C$_8$-alkenyloxy, substituted or non-substituted C$_4$-C$_8$-alkynyloxy, alkynyloxy, substituted or non-substituted aryl, or substituted or non-substituted heterocyclyl.

6. A compound according to claim 1 wherein Q represents a C$_5$-C$_{12}$-benzofused hetercyclyl.

7. A compound according to claim 1 wherein Z$^2$, Z$^3$ and Z$^4$ independently represent a hydrogen atom, a halogen atom, or substituted or non-substituted C$_1$-C$_8$-alkyl.

8. A compound according to claim 1 wherein Y$^1$ to Y$^5$ each represents a hydrogen atom.

9. A compound according to claim 1 wherein Q represents 3,4-dihydro-2H-chromen-2-yl.

10. A compound of formula (I) according to claim 1

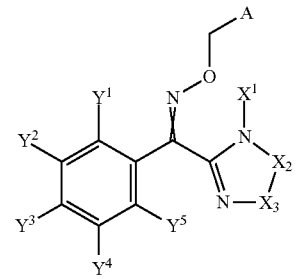

(I)

and/or a salt, N-oxide, metallic complex, and/or metalloidic complex thereof and/or an (E) and/or (Z) isomer and/or a mixture thereof, wherein A is

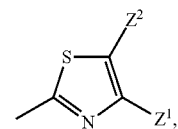

X$^1$ is methyl, X$^2$ is CO, X$^3$ is O, Y$^1$ is hydrogen, Y$^2$ is hydrogen, Y$^3$ is hydrogen, Y$^4$ is hydrogen, Y$^5$ is hydrogen, Z$^1$ is (3,4-dihydro-2H-chromen-2-ylcarbonyl)amino, and Z$^2$ is hydrogen.

* * * * *